(12) United States Patent
Aravamudan et al.

(10) Patent No.: US 12,144,634 B1
(45) Date of Patent: Nov. 19, 2024

(54) APPARATUS AND A METHOD FOR THE IMPROVEMENT OF ELECTROCARDIOGRAM VISUALIZATION

(71) Applicant: Anumana, Inc., Cambridge, MA (US)

(72) Inventors: Murali Aravamudan, Andover, MA (US); Venkataraman Soundarajan, Andover, MA (US); Rakesh Barve, Bengaluru (IN); Michiel Jm Niesen, San Diego, CA (US); Arjun Puranik, San Jose, CA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/229,033

(22) Filed: Aug. 1, 2023

(51) Int. Cl.
| | |
|---|---|
| *A61B 5/31* | (2021.01) |
| *A61B 5/00* | (2006.01) |
| *A61B 5/341* | (2021.01) |
| *A61B 5/343* | (2021.01) |
| *G16H 50/20* | (2018.01) |
| *G16H 50/70* | (2018.01) |

(52) U.S. Cl.
CPC ............ *A61B 5/341* (2021.01); *A61B 5/343* (2021.01); *A61B 5/7253* (2013.01); *G16H 50/20* (2018.01); *G16H 50/70* (2018.01)

(58) Field of Classification Search
CPC ....... A61B 5/341; A61B 5/343; A61B 5/7253; G16H 50/70; G16H 50/20
USPC ........................................................ 600/512
See application file for complete search history.

(56) References Cited

U.S. PATENT DOCUMENTS

| | | | |
|---|---|---|---|
| 9,451,890 B2* | 9/2016 | Gitlin .................. | A61B 5/0006 |
| 11,475,570 B2* | 10/2022 | Krummen .............. | A61B 5/684 |
| 2003/0083586 A1* | 5/2003 | Ferek-Petric .......... | A61B 5/363 |
| | | | 600/512 |
| 2006/0235322 A1* | 10/2006 | Simske .................. | A61B 5/341 |
| | | | 600/512 |
| 2015/0238101 A1* | 8/2015 | Weng .................. | A61N 1/3987 |
| | | | 600/512 |

(Continued)

FOREIGN PATENT DOCUMENTS

| | | | | |
|---|---|---|---|---|
| CN | 1994221 A | * | 7/2007 | |
| ES | 2606216 T3 | * | 3/2017 | ......... A61B 5/04011 |

(Continued)

*Primary Examiner* — Michael J Lau
(74) *Attorney, Agent, or Firm* — Caldwell Intellectual Property Law

(57) ABSTRACT

An apparatus for the improvement of electrocardiogram visualization is disclosed. The apparatus includes at least a processor and a memory communicatively connected thereto. The memory instructs the processor to receive a plurality of electrocardiogram signals, wherein the plurality of electrocardiogram signals is generated using at least one sensor of a plurality of sensors connected to a patient, to receive at least one transformation matrix, and to transform the plurality of electrocardiogram signals into a cardiac vector as a function of the at least one transformation matrix. The memory instructs the processor to generate a vectorcardiogram image as a function of the cardiac vector, wherein the vectorcardiogram image comprises a representation of the cardiac vector in a three-dimensional (3D) space. The memory instructs the processor to assign at least one diagnostic label to the patient as a function of the vectorcardiogram image.

16 Claims, 13 Drawing Sheets

(56) References Cited

U.S. PATENT DOCUMENTS

| | | | |
|---|---|---|---|
| 2015/0366478 A1* | 12/2015 | Vranic | A61B 5/352 |
| | | | 600/512 |
| 2016/0015286 A1* | 1/2016 | Gitlin | A61N 1/36514 |
| | | | 600/512 |
| 2017/0209698 A1* | 7/2017 | Villongco | G16H 50/50 |
| 2019/0282178 A1* | 9/2019 | Volosin | A61B 5/0022 |
| 2019/0282823 A1* | 9/2019 | Freeman | A61N 1/3993 |
| 2019/0328457 A1* | 10/2019 | Villongco | G16H 40/67 |
| 2019/0332729 A1* | 10/2019 | Villongco | G06F 30/20 |
| 2019/0333643 A1* | 10/2019 | Villongco | A61B 5/319 |
| 2020/0037907 A1* | 2/2020 | van Dam | A61B 5/0013 |
| 2021/0038319 A1* | 2/2021 | Villongco | A61B 5/7246 |
| 2023/0049769 A1* | 2/2023 | Villongco | G06N 3/0464 |

FOREIGN PATENT DOCUMENTS

| | | | | |
|---|---|---|---|---|
| WO | WO-2004089210 A1 * | 10/2004 | | A61B 5/0452 |
| WO | WO-2012027969 A1 * | 3/2012 | | A61B 5/04011 |
| WO | WO-2020101864 A1 * | 5/2020 | | A61B 18/1492 |
| WO | WO-2020142539 A1 * | 7/2020 | | A61B 5/361 |

* cited by examiner

APPARATUS AND A METHOD FOR THE IMPROVEMENT OF ELECTROCARDIOGRAM VISUALIZATION

FIELD OF THE INVENTION

The present invention generally relates to the field of transformed visualization of an electrocardiogram. In particular, the present invention is directed to an apparatus and a method for the improvement of electrocardiogram visualization.

BACKGROUND

Electrocardiography a valuable tool for assessing cardiac function and diagnosing various cardiac conditions. Traditional methods for interpreting ECG signals involve manual analysis by trained healthcare professionals, which can be time-consuming and subject to inter-observer variability. There is a need for an automated system that can efficiently analyze ECG signals and assign accurate diagnostic labels, aiding in timely and reliable cardiac disease diagnosis.

SUMMARY OF THE DISCLOSURE

In an aspect, an apparatus for the improvement of electrocardiogram visualization is disclosed. The apparatus includes at least a processor and a memory communicatively connected to the at least a processor. The memory instructs the processor to receive a plurality of electrocardiogram signals, wherein the plurality of electrocardiogram signals is generated using at least one sensor of a plurality of sensors connected to a patient. The memory instructs the processor to receive at least one transformation matrix. The memory instructs the processor to transform the plurality of electrocardiogram signals into a cardiac vector as a function of the at least one transformation matrix. The memory instructs the processor to generate a vectorcardiogram image as a function of the cardiac vector, wherein the vectorcardiogram image comprises a representation of the cardiac vector in a three-dimensional (3D) space. The memory instructs the processor to assign at least one diagnostic label to the patient as a function of the vectorcardiogram image.

In another aspect, a method for the improvement of electrocardiogram visualization is disclosed. The method includes receiving, using at least a processor, a plurality of electrocardiogram signals, wherein the plurality of electrocardiogram signals is generated using at least one sensor of a plurality of sensors connected to a patient. The method includes receiving, using at least a processor, at least one transformation matrix. The method includes transforming, using the at least a processor, the plurality of electrocardiogram signals into a cardiac vector as a function of the at least one transformation matrix. The method includes generating, using the at least a processor, a vectorcardiogram image as a function of the cardiac vector, wherein the vectorcardiogram image comprises a representation of the cardiac vector in a three-dimensional (3D) space. The method includes assigning, using the at least a processor, at least one diagnostic label to the patient as a function of the vectorcardiogram image.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and a method for the improvement of electrocardiogram visualization is disclosed. The apparatus includes at least a processor and a memory communicatively connected to the at least a processor. The memory instructs the processor to receive a plurality of electrocardiogram signals and a patient profile from a patient. The memory instructs the processor to transform the plurality of electrocardiogram signals into a cardiac vector. The memory instructs the processor to generate a vectorcardiogram image as a function of the cardiac vector. The memory instructs the processor to assign at least one diagnostic label to the patient as a function of the vectorcardiogram image and the patient profile. The memory instructs display the at least one diagnostic label using a display device. Exemplary embodiments illustrating aspects of the present disclosure are described below in the context of several specific examples.

Figure 1:
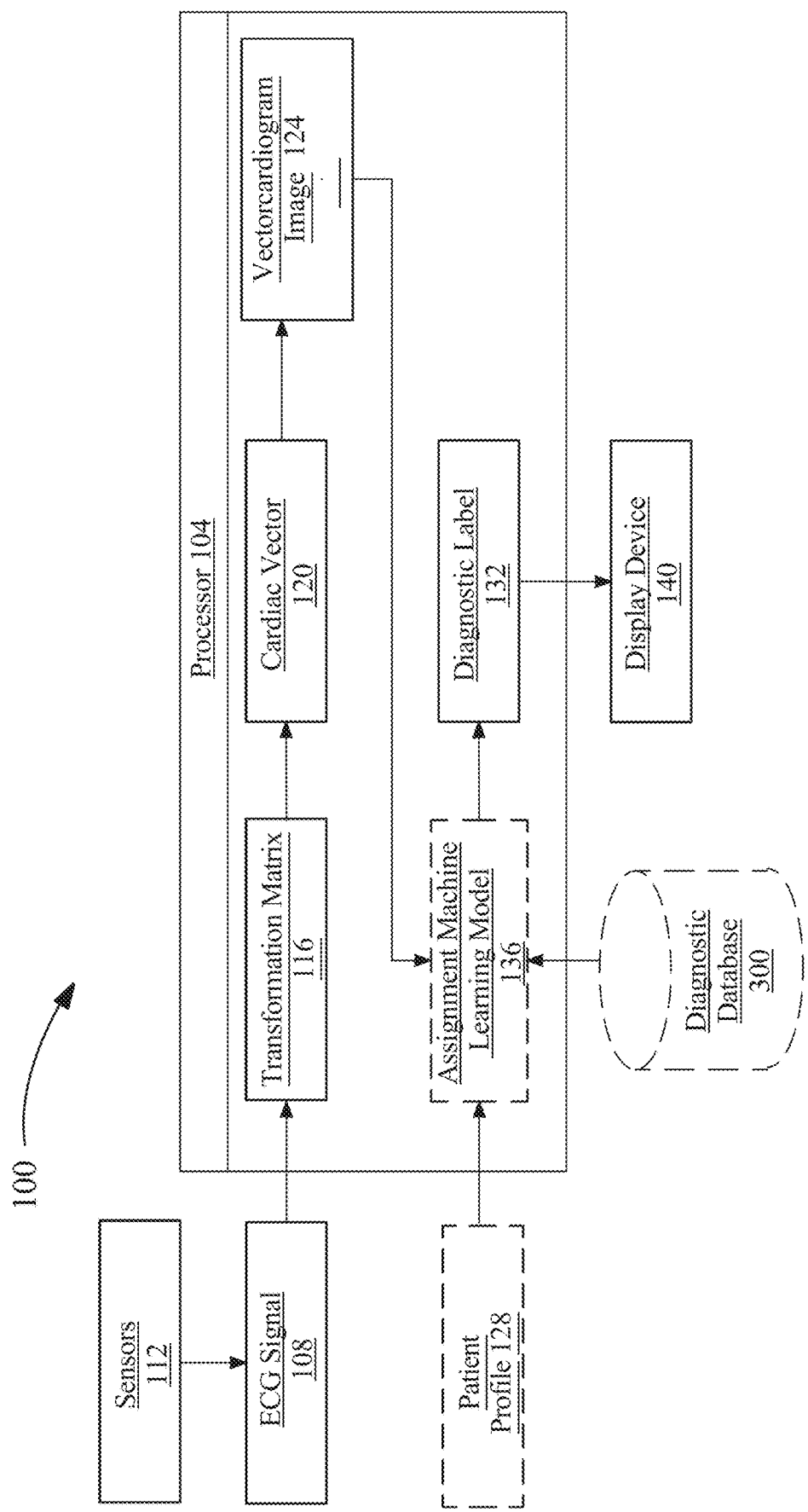
FIG. 1 is a block diagram of an exemplary embodiment of an apparatus for the improvement of electrocardiogram visualization.

Referring now to FIG. 1, an exemplary embodiment of an apparatus 100 for the improvement of electrocardiogram visualization is illustrated. Apparatus 100 includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory. Memory is communicatively connected to processor 104. Memory may contain instructions configuring processor 104 to perform tasks disclosed in this disclosure. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 is configured to receive a plurality of electrocardiogram(ECG) signals 108 from a patient. As used in the current disclosure, a "electrocardiogram signal" is a signal representative of electrical activity of heart. The ECG signal 108 may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves provide information about the duration and regularity of various phases of the cardiac cycle. The ECG signal can help diagnose various heart conditions, such as arrhythmias, myocardial infarction (heart attack), conduction abnormalities, and electrolyte imbalances. In an embodiment, each sensor 112 may generate an individual ECG signal 108.

With continued reference to FIG. 1, the plurality of electrocardiogram signals captures a temporal view of cardiac electrical activities. A "temporal view," as used in the current disclosure, refers to the analysis and visualization of heart-related events and phenomena over time. A temporal view may include patterns, changes, and dynamics of cardiac activity over time. A temporal view may include information surrounding the rhythm of the heart, including the regularity or irregularity of heartbeats. It allows for the identification of various rhythm abnormalities such as tachycardia (fast heart rate), bradycardia (slow heart rate), or arrhythmias (irregular heart rhythms). A temporal view of cardiac activities in three dimensions may refer to a visualization that represents the temporal evolution of cardiac events or phenomena in a three-dimensional space. It provides a comprehensive understanding of how various cardiac activities change over time. The ECG signal 108 may move through the 3D space of the heart over time. The signal does not just move forward in time, it also moves through the physical space of the heart, from SA node through atria, to AV node, and then through the ventricles. Such movement of the electrical signal through the heart's physical space over time can be referred to as "spatiotemporal excitation and propagation" which could be captured by plurality of ECG signals 108. It is an essentially a way of observing and analyzing the timing and sequence of the heart's electrical activity as it moves through the physical structure of the heart. In the current case the dimensions may include axis representing time, spatial dimensions, and cardiac activity. By combining the temporal, spatial, and cardiac activity dimensions, the temporal view of cardiac activities in three dimensions allows for a comprehensive visualization and analysis of dynamic changes occurring within the heart. It can be used to study phenomena like electrical conduction, ventricular wall motion, valve function, blood flow dynamics, or the interaction between different regions of the heart. This visualization approach provides valuable insights into the complex temporal dynamics of cardiac activities and aids in understanding cardiac function, pathology, and treatment evaluation.

With continued reference to FIG. 1, the plurality of electrocardiogram signals 108 are generated using at least a sensor 112. As used in this disclosure, a "sensor" is a device that is configured to detect an input and/or a phenomenon and transmit information related to the detection. Sensor 112 may detect a plurality of data. A plurality of data detected by sensor 11 may include, but is not limited to, electrocardiogram signals 108, heart rate, blood pressure, electrical signals related to the heart, and the like. In one or more embodiments, and without limitation, sensor 112 may include a plurality of sensors 112. In one or more embodiments, and without limitation, sensor 112 may include one or more electrodes, and the like. Electrodes used for an electrocardiogram (ECG) are small sensors or conductive patches that are placed on specific locations on the body to detect and record the electrical signals generated by the heart. Senor 112 serves as the interface between the body and the ECG machine, allowing for the measurement and recording of the heart's electrical activity. A plurality of sensors 112 may include 10 electrodes used for a standard 12-lead ECG, placed in specific positions on the chest and limbs of the patient. These electrodes are typically made of a conductive material, such as metal or carbon, and are connected to lead wires that transmit the electrical signals to the ECG machine for recording. Proper electrode placement is crucial to ensure accurate signal detection and recording.

With continued reference to FIG. 1, the plurality of sensors 112 may be placed on each limb, wherein there may be at least one sensor 112 on each arm and leg. These sensors 112 may be labeled I, II, III, V1, V2, V3, V4, V5, V6, and the like. For example, Sensor I may be placed on the left arm, Sensor II may be placed on the right arm, and Sensor III may be placed on the left leg. Additionally, a plurality of sensors 112 may be placed on various portions of the patient's torso and chest. For example, a sensor V1 may be placed in the fourth intercostal space at both the right sternal borders and sensor V2 may be fourth intercostal space at both the left sternal borders. A sensor V3 may also be placed between sensors V2 and V4, halfway between their positions. Sensor V4 may be placed in the fifth intercostal space at the midclavicular line. Sensor V5 may be placed horizontally at the same level as sensor V4 but in the anterior axillary line. Sensor V6 may be placed horizontally at the same level as V4 and V5 but in the midaxillary line.

With continued reference to FIG. 1, the plurality of sensors 112 may include augmented unipolar sensors. These sensors 112 may be labeled as aVR, aVL, and aVF. These sensor may be derived from the limb sensors and provide additional information about the heart's electrical activity. These leads are calculated using specific combinations of the limb leads and help assess the electrical vectors in different orientations. For example, aVR may be derived from Sensor II and Sensor III. In another example, aVL may be derived from sensor I and Sensor III. Additionally, aVF may be derived from Lead I and Lead II. The combination of limb sensors, precordial sensors, and augmented unipolar sensors allows for a comprehensive assessment of the heart's electrical activity in three dimensions. These leads capture the electrical signals from different orientations, which are then transformed into transformed coordinates to generate vectorcardiogram (VCG) representing magnitude and direction of electrical vectors during cardiac depolarization and repolarization. Transformed coordinates may include one or more a Cartesian coordinate system $(x, y, z)$, polar coordinate system $(r, \theta)$, cylindrical coordinate system $(p, q, z)$, or spherical coordinate system $(r, \theta, q)$. In some cases, transformed coordinates may include an angle, such as with polar coordinates, cylindrical coordinates, and spherical coordinates. In some cases, VCG may be normalized thus permitting full representation with only angles, i.e., angle traversals. In some cases, angle traversals may be advantageously processed with one or more processes, such as those described below and/or spectral analysis.

With continued reference to FIG. 1, processor 104 is configured to receive at least one transformation matrix 116. A "transformation matrix," for the purpose of this disclosure, is a mathematical tool used to perform transformations on objects in a coordinate system. It may include operations such as, without limitation, rotation, scaling, shearing, and translation (moving the whole object without changing its shape or orientation). In a non-limiting example, the transformation matrix may be used to map the information from the 12-lead ECG system into the 3-lead VCG system. Processor may apply a linear transformation to plurality of ECG signals, wherein the application of the linear transformation may effectively change the basis of the coordinate system from the 12-lead ECG to the 3-lead VCG. In the field of vectorcardiography (VCG), the transformation matrix can play a role in mapping information from one system to another. For instance, a common example is mapping data from the 12-lead electrocardiogram (ECG) system to the 3-lead VCG system. In this scenario, the transformation matrix is applied to a set of ECG signals in order to effectively change the basis of the coordinate system from the 12-lead ECG to the 3-lead VCG. In a non-limiting example, the ECG signals may be represented by a matrix of dimensions 5000×12, with 5000 samples and 12 leads or sensors 112. The transformation matrix would have dimensions 12×3, representing the transformation from the 12-lead ECG system to the 3-lead VCG system. By multiplying the ECG matrix with the transformation matrix, the resulting matrix would have dimensions 5000×3, corresponding to the transformed VCG signals. The linear transformation performed by the matrix effectively changes the basis of the coordinate system, allowing the representation of the data in a different format or perspective. This transformation process facilitates the conversion of ECG information to the VCG system, enabling further analysis and interpretation based on the specific requirements and advantages of the VCG approach.

With continued reference to FIG. 1, a transformation matrix 116 includes a selection of at least one lead system. As used in the current disclosure, a "lead system" is a configuration of electrodes placed on the body to measure and record electrical signals. A lead system may be used to capture the electrical activity of the heart or other physiological signals. The placement and arrangement of the electrodes in lead system determine the specific views or angles from which the electrical signals are recorded. In an embodiment, a lead system may be designed to provide a two-dimensional representation of the heart's electrical activity. It may consist of multiple leads placed on specific locations on the body to measure electrical potentials in different directions. A lead systems 116 may use various arrangements of a plurality of sensors 112, which may include placing sensors 112 on limbs and the precordial area. Examples of lead systems may include a frank lead system, mason-likar lead system, XYZ lead system, dower lead system, first lead system, and the like. The sensors 112 placed on the limbs may be used to capture the electrical activity in the frontal plane, while sensors 112 in the precordial area provide information about the electrical activity in the horizontal plane. In another embodiment, a lead system may be specifically designed to capture and represent the three-dimensional nature of the heart's electrical activity. It involves using multiple electrodes positioned on the body to measure electrical vectors from different angles. Processor 104 may identify the location of each sensor 112 based on a manual input from a medical professional. Alternatively, processor 104 may identify the location of each sensor based on the types.

With continued reference to FIG. 1, a lead system may include a first lead system. As used in the current disclosure, a "first lead system" is a group of sensors 112 in that are positioned on the frontal plane (X-plane), the horizontal plane (Y-plane), and the coronal plane (Z-plane). These leads provide information about the heart's electrical activity from different perspectives and angles. The X-plane may refer to the imaginary plane that is perpendicular to the Y-plane of the body. In some embodiments, the X-plane may alternatively be labeled as the transvers plane. Sensors 112 located on the X-plane may be positioned along the midpoint between the two shoulders of the patient. Sensors 112 along the X-plane may capture the electrical activity in the anterior-posterior direction, representing the movement of electrical vectors from the front to the back of the body. The Y-plane is oriented in the right-left direction of the body. The Y-plane may be labeled as the sagittal plane or longitudinal plane. Sensors 112 along the Y-plane may detect movement of electrical vectors from the right side to the left side of the body. The sensors 112 position along the y-plane may be positioned on the midpoint between the jugular notch (suprasternal notch) and the umbilicus (at the xiphoid process) on the anterior midline of the body. By recording the electrical signals along the Y-plane, the sensors 112 provide information about the spatial orientation and movement of electrical vectors in the right-left direction.

With continued reference to FIG. 1, processor 104 is configured to transform plurality of electrocardiogram signals 108 into a cardiac vector 120 as a function of the transformation matrix 116. As used in the current disclosure, a "cardiac vector" is a transformed vector representative of an electrocardiogram, for example a three-dimensional vector containing information about magnitude and direction of electrical signals generated by heart during its depolarization and repolarization processes. A single cardiac vector 120 may be represented by the magnitude and direction of a plurality of ECG signals 108 generated from various sensor 112 located on the patient. The cardiac vector 120 may represent the net electrical forces generated by the heart at a specific point in time. It has three components along three orthogonal axes: X, Y, and Z. The X-axis component may represent the anterior-posterior direction. It indicates the movement of electrical vectors from the front (anterior) to the back (posterior) of the heart. The Y-axis component may represent the right-left direction. It indicates the movement of electrical vectors from the right side to the left side of the heart. The Z-axis component may represent the superior-inferior direction. It indicates the movement of electrical vectors from the top (superior) to the bottom (inferior) of the heart. The magnitudes of these three components may determine the length of the cardiac vector, while their directions indicate the orientation of the vector in three-dimensional space. By analyzing the three-dimensional cardiac vector 120 over time, processor 104 can gain insights into the spatial orientation and sequence of the heart's electrical activity. This helps in diagnosing various cardiac conditions, assessing the spread of electrical impulses, and evaluating the overall electrical function of the heart.

With continued reference to FIG. 1, processor 104 may generate a cardiac vector 120 by transforming an ECG signal 108 into transformed coordinates using the transformation matrix 116. The transformed coordinates represent the magnitude and direction of the electrical vectors in three dimensions. The transformation process may vary based on the lead system and the transformation matrix 116 that is being used. The ECG signals 108 are transformed to obtain transformed coordinates. The transformation equations may differ depending on the lead system and the transformation matrix 116 being used. In a non-limiting example, in the first lead system, the standard Cartesian and/or polar transformation equations are used to derive the transformed coordinates from sensors 112 (I, II, and III) and sensors 112 (V1 to V6). These equations involve specific combinations of lead signals and coefficients. Using the transformed coordinates, the ECG signals 108 or each point in time are reconstructed in three-dimensional space. These cardiac vector 120 represent the direction and magnitude of the electrical activity at that specific moment during the cardiac cycle. In a non-limiting example, using the first lead system, the following processes to obtain the X, Y, and Z coordinates. When generating the X coordinates an ECG signal 108 from sensors 112 represented by I, II, III, aVR, aVL, aVF may be used. An example for the transformation equation within the transformation matrix 116 for the X-axis may include: $X=(0.3333*(aVR-aVL))$. When generating the Y coordinates, an ECG signal 108 from sensors 112 represented by I, II, III, aVR, aVL, aVF may be used. An example for the transformation equation within the transformation matrix 116 for the Y-axis may include: $Y=(0.3333*(I+aVR+aVL))$. When generating the Z coordinates, an ECG signal 108 from sensors 112 represented by I, II, III, aVR, aVL, aVF and V1 to V6 may be used. An example for the transformation equation within the transformation matrix 116 may include: Z=(0.1667*(I+II+III+aVR+aVL+aVF+V3+V4−V5−V6)). These equations involve specific combinations of lead signals with different coefficients to calculate the X, Y, and Z coordinates. The coefficients are derived based on the principles of vectorcardiography and the orientation of the leads in the first lead system.

With continued reference to FIG. 1, processor 104 may generate a cardiac vector 120 by combining transformed coordinates from multiple sensors 112. The combination may involve adding the X, Y, and Z components of each ECG signal 108 to obtain the resultant X, Y, and Z components of the cardiac vector 120. The X, Y, and Z coordinates obtained from each ECG signal 108 are summed to calculate the overall X, Y, and Z components of the cardiac vector. This summation is performed by adding the corresponding values of X, Y, and Z from each sensor 112. This may include adding the X, Y, and Z coordinates from all the sensors 112 to obtain the resultant X, Y, and Z components of the cardiac vector 120. Using the resultant X, Y, and Z components obtained from the summation, the overall cardiac vector 120 is calculated. The cardiac vector 120 represents the net electrical forces generated by the heart at a specific point in time. The magnitude of the cardiac vector 120 may be determined by calculating the vector length using the Pythagorean theorem. For example, the magnitude may be calculated using a formula consisting of Magnitude=sqrt(X^2+Y^2+Z^2). The direction of the cardiac vector 120 may be determined by the orientation of the X, Y, and Z components in three-dimensional space. By combining the transformed coordinates obtained from multiple leads and calculating the overall cardiac vector 120, processor 104 can gain insights into the magnitude, direction, and orientation of the heart's electrical activity during its depolarization and repolarization processes.

With continued reference to FIG. 1, processor 104 may transform the plurality of electrocardiogram signals 108 into a cardiac vector 120 using a vector machine-learning model. As used in the current disclosure, a "vector machine machine-learning model" is a machine-learning model that is configured to generate a cardiac vector 120. Vector machine machine-learning model may be consistent with the machine-learning model described below in FIG. 2. Inputs to the vector machine machine-learning model may include an ECG signal 108, lead system, transformation matrix 116, transformed components, examples of cardiac vectors 120, and the like. Outputs to the vector machine machine-learning model may include cardiac vectors 120 tailored to the electrocardiogram signals 108. Alternatively, outputs to the vector machine machine-learning model may include Cartesian and/or polar components associated with the cardiac vectors 120. Vector training data may include a plurality of data entries containing a plurality of inputs that are correlated to a plurality of outputs for training a processor by a machine-learning process. In an embodiment, vector training data may include a plurality of electrocardiogram signals 108 correlated to examples of cardiac vectors 120. Vector training data may be received from database 300. Vector training data may contain information about ECG signal 108, lead system, transformation matrix 116, Cartesian and/or polar components, examples of cardiac vectors 120, and the like. In an embodiment, vector training data may be iteratively updated as a function of the input and output results of past vector machine machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model.

With continued reference to FIG. 1, processor 104 may be configured to generate a vectorcardiogram image 124 as a function of the cardiac vector 120. As used in the current disclosure, a "vectorcardiogram image" is a representation of at least a cardiac vector 120, which may or may not be a graphical representation but which may be visualized for display. The vectorcardiogram image 124 may be a graphical representation of the cardiac vector 120 over time. Placed in other words the vectorcardiogram image 124 includes a plot of the cardiac vector 120 over a given time period, such as the cardiac cycle. The vectorcardiogram image 124 provides a visual depiction of the magnitude and direction of the electrical vectors generated by the heart during its depolarization and repolarization processes over time. A vectorcardiogram image 124 may include a Cartesian and/or polar axes. The vectorcardiogram image 124 is plotted in a three-dimensional coordinate system, where the X-axis represents the anterior-posterior direction, the Y-axis represents the right-left direction, and the Z-axis represents the superior-inferior direction. These axes provide a spatial reference for the magnitude and direction of the cardiac vectors. A vectorcardiogram image 124 may be described as a graphical representation of the cardiac vector 120, displaying the cardiac vector 120 over a period of time. In some cases, the time period may extend across several heart beats or a cardiac cycle. In some cases, the vectorcardiogram image 124 may include annotations of the P-wave, QRS complex, and T-wave, which are the characteristic waveforms of the electrical activity of the heart. These waveforms represent the depolarization and repolarization of the atria and ventricles. The placement and orientation of these waveforms within the vector loop provides information about the spatial distribution and sequence of the electrical activity.

With continued reference to FIG. 1, the vectorcardiogram image 124 may include a vector loop. As used in the current disclosure, a "vector loop" is a graphical representation of the trajectory followed by the cardiac vector during the cardiac cycle. It illustrates the changes in the magnitude and direction of the electrical vectors generated by the heart as it undergoes depolarization and repolarization. The vector loop is a continuous curve that connects the Cartesian and/or polar coordinates obtained from different leads or electrodes throughout the cardiac cycle. It illustrates the changes in the magnitude and direction of the electrical vectors during each phase of the heart's electrical activity. The vector loop is typically plotted in a two-dimensional plane, although it represents the three-dimensional nature of the cardio vector 120. The X and Y axes of the plot correspond to the anterior-posterior and right-left directions, respectively. The vector loop is created by connecting the points that represent the X and Y coordinates of the cardiac vector 120 at each moment in time. The shape and characteristics of the vector loop provide valuable information about the electrical activity of the heart. The vector loop can take various shapes depending on the orientation and magnitude of the cardiac vector 120 during different phases of the cardiac cycle. The loop may be asymmetrical or irregular, reflecting abnormalities in the electrical conduction system or underlying cardiac conditions. The size of the vector loop represents the magnitude or strength of the electrical vectors generated by the heart. A larger loop indicates a greater magnitude of electrical activity, while a smaller loop suggests a weaker or altered electrical conduction. The orientation of the vector loop reflects the spatial direction of the electrical vectors. The loop may rotate or change its orientation during different phases of the cardiac cycle, providing information about the sequential activation and propagation of electrical impulses within the heart. Deviations of the vector loop from the normal axis indicate abnormalities in the heart's electrical conduction system. Axis deviations can provide valuable diagnostic information, such as identifying the presence of left ventricular hypertrophy or bundle branch blocks.

With continued reference to FIG. 1, the vectorcardiogram image 124 may include a time-dependent depiction of the cardiac vector. A time-dependent depiction of a cardiac vector refers to a graphical representation that shows the direction and magnitude of the electrical activity within the heart at a specific moment in time. This depiction is often visualized using a vector arrow or line, representing the vector of electrical forces generated by the heart. A time-dependent depiction of the cardiac vector 120 may provide valuable information about the electrical activation and conduction patterns of the heart. It helps clinicians assess the overall electrical axis and the spatial orientation of the heart's electrical activity. In an embodiment, a time-dependent cardiac vector depiction may be displayed as a vector loop or a sequence of vector arrows. The vector loop is a closed curve that represents a complete cardiac cycle, showing the changes in the electrical vector throughout the cardiac cycle. It displays the direction and magnitude of the electrical forces generated by the heart in three-dimensional space. The starting point of the vector loop is often referred to as the origin, and subsequent points along the loop may represent different time intervals during the cardiac cycle. The vector arrows connecting these points indicate the magnitude and direction of the electrical forces at those specific moments. The length and direction of the arrows convey information about the amplitude and orientation of the electrical vector. A time-dependent depiction of a cardiac vector may include video of the cardiac vector. Additionally, when renditions of contiguous time slices are transformed into a video, the evolution of the spatial representation shape of each time slice over time not only reduces the cognitive overload of feature extraction by humans but also improves the ability to detect anomalies that are spread across both a single lead and multiple leads collectively over time.

With continued reference to FIG. 1, vectorcardiogram image 124 may include displaying the cardiac vector 120 through an alternative lag-reconstructed ECG representation. As used in the current disclosure, an "alternative lag-reconstructed ECG representation" is a method used to analyze and visualize the electrical activity of the heart by reconstructing the ECG signal using time-delayed versions of itself. This approach is based on the concept that the dynamics of the cardiac electrical system can be captured by examining the relationship between different time points within the ECG waveform. Instead of representing the ECG signal in the traditional format of voltage or amplitude over time, the lag-reconstructed representation may focus on creating a multidimensional space using delayed versions of the original ECG signal. Each dimension in this space corresponds to a time-delayed version of the ECG waveform. To create a lag-reconstructed ECG representation, a technique called time-delay embedding is typically employed. It involves selecting a suitable time delay parameter and embedding dimension. The time delay determines how far apart the time points in the reconstructed signal are, and the embedding dimension determines the number of delayed versions used for reconstruction. By reconstructing the ECG signal in this manner, it becomes possible to capture and visualize the underlying dynamics and nonlinear properties of the cardiac electrical activity. This approach is particularly useful for analyzing and detecting patterns related to cardiac arrhythmias, heart rate variability, and other complex dynamics that may not be readily apparent in the traditional ECG representation. Once the lag-reconstructed ECG representation is obtained, various techniques such as phase space analysis, recurrence plots, or nonlinear dynamics methods can be applied to analyze and interpret the reconstructed signal. These methods can reveal information about the underlying dynamics, attractors, or recurrence patterns, which may provide insights into the cardiac system's behavior. Processor 104 may generate an alternative lag-reconstructed ECG representation by choosing appropriate time delay, which determines the separation between the time-delayed copies of the ECG signal. This time delay is often determined using techniques such as the mutual information or autocorrelation function. Processor 104 may generate lag vectors as a function of the time delay. Lag vectors may be created by taking successive samples of the ECG signal at the chosen time delay. These lag vectors, also known as delay vectors, represent points in the reconstructed phase space. The embedding dimension refers to the number of components or variables used to construct each lag vector. It is often estimated using techniques such as the false nearest neighbors or correlation dimension. Once the lag vectors are constructed, they can be visualized in the reconstructed phase space. The resulting trajectory or attractor in the phase space can provide insights into the underlying dynamics of the ECG signal. Various nonlinear analysis techniques, such as fractal dimension estimation, recurrence quantification analysis, or Lyapunov exponent calculation, can be applied to analyze the reconstructed phase space and extract relevant information.

With continued reference to FIG. 1, the vectorcardiogram image 124 may include a color-coded cardiac vector. In an embodiment, a color-coded cardiac vector may be generated as a function the properties the cardiac vector. The cardiac vector may be color-coded as a function to a temporal view of the cardiac vector. Processor 104 may assign different colors to the cardiac vector based on various dynamic characteristics or properties derived from the temporal view of electrical activities, such as the ECG signal. This color-coded representation enhances the visualization and understanding of the underlying dynamics of the cardiac vector. Examples of properties that may be used to assign colors to the cardiac vectors may include magnitude or amplitude, direction or orientation, direction or orientation, complexity or irregularity, and the like. The amplitude of the cardiac vector represents the strength or intensity of the electrical activity. Color-coding the vector may be based on amplitude and can provide information about the relative strength of the electrical forces at different points in time, potentially indicating areas of increased or decreased electrical activity. The direction of the cardiac vector signifies the spatial orientation of the electrical forces within the heart. Color-coding based on direction may reveal patterns or changes in the orientation of the electrical activity, aiding in the identification of specific cardiac abnormalities or conduction patterns. The velocity or speed of the cardiac vector may reflect the rate at which the electrical activity is propagating. Color-coding based on velocity may highlight areas of rapid or slow conduction, helping to identify regions with abnormal conduction velocities or disturbances in the electrical activation sequence. Dynamical properties related to the complexity or irregularity of the cardiac vector can be used for color-coding. Measures such as fractal dimension, entropy, or complexity indices can be utilized to quantify the complexity or irregularity of the vector's behavior. Color-coding based on these properties can aid in identifying chaotic or non-linear dynamics within the electrical activity.

With continued reference to FIG. 1, one or more of ECG signal 108, cardiac vector 120, and vectorcardiogram image 124 may be represented as at least a signal. As used in this disclosure, a "signal" is any intelligible representation of data, for example from one device to another. A signal may include an optical signal, a hydraulic signal, a pneumatic signal, a mechanical signal, an electric signal, a digital signal, an analog signal and the like. In some cases, a signal may be used to communicate with a computing device, for example by way of one or more ports. In some cases, a signal may be transmitted and/or received by a computing device for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

Still referring to FIG. 1, in some cases, system 100 (e.g., processor 104 and/or sensors 112) may perform one or more signal processing steps on a signal, such as ECG signal 108, cardiac vector 120, or vectorcardiogram image 124. For instance, system 100 may analyze, modify, and/or synthesize a signal representative of data in order to improve the signal, for instance by improving transmission, storage efficiency, or signal to noise ratio. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which vary continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued and complex-valued, multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

With continued reference to FIG. 1, processor 104 may generate vectorcardiogram image 124 using a transformation machine-learning model. As used in the current disclosure, a "transformation machine machine-learning model" is a machine-learning model that is configured to generate a vectorcardiogram image 124. Transformation machine machine-learning model may be consistent with the machine-learning model described below in FIG. 2. Inputs to the transformation machine machine-learning model may include an ECG signal 108, lead system, transformed coordinates, cardiac vector 120, examples of vectorcardiogram image 124, and the like. Outputs to the transformation machine machine-learning model may include vectorcardiogram image 124 tailored to the cardiac vector 120. Alternatively, outputs to the transformation machine machine-learning model may include a vector loop. Transformation training data may include a plurality of data entries containing a plurality of inputs that are correlated to a plurality of outputs for training a processor by a machine-learning process. In an embodiment, transformation training data may include a plurality of cardiac vectors 120 correlated to examples of vectorcardiogram image 124. Transformation training data may be received from database 300. Transformation training data may contain information about ECG signal 108, lead system, transformed coordinates, cardiac vector 120, examples of vectorcardiogram image 124, and the like. In an embodiment, transformation training data may be iteratively updated as a function of the input and output results of past transformation machine machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model.

With continued reference to FIG. 1, processor 104 may be configured to receive a patient profile 128 from a patient. For the purposes of this disclosure, a "patient profile" is a representation of information and/or data describing information associated with a patient. A patient profile 128 may be made up of a plurality of patient data 112. As used in the current disclosure, "patient data" is information associated with the patient. A patient profile 128 may be created by a processor 104, a patient, or received from a database such as database 300. The patient profile 128 may include the personal information of the patient such as age, height, gender, weight, current medical conditions, family medical conditions, medical history, and the like. Patient data 112 may include health data. As used in the current disclosure, "health data" is an element of data that is related to a patient's current health. Health data may include test results, medical records, family medical history, list of medical conditions, physician notes, medical facility records, and the like. A patient profile may be placed through an encryption process for security purposes. A patient profile 128 may include patient records. As used in the current disclosure, a "patient record" is a document that contains information regarding the patient. Patient records may include medical records, family history, medical surveys, government records (i.e., birth certificates, social security cards, and the like), and the like. Patient records may include a variety of types of "notes" entered over time by the patient, medical personnel, third-parties and the like.

With continued reference to FIG. 1, a patient profile 128 may be received by process 104 via patient input. For example, and without limitation, the patient or a third party may manually input patient profile 128 using a graphical patient interface of processor 104 or a remote device, such as for example, a smartphone or laptop. The patient profile 128 may additionally be generated via the answer to a series of questions. The series of questions may be implemented using a chatbot, as described herein below. A chatbot may be configured to generate questions regarding any element of the patient profile 128. In a non-limiting embodiment, a patient may be prompted to input specific information or may fill out a questionnaire. In an embodiment, a graphical patient interface may display a series of questions to prompt a patient for information pertaining to the patient profile 128. The patient profile 128 may be transmitted to processor 104, such as via a wired or wireless communication, as previously discussed in this disclosure.

With continued reference to FIG. 1, processor 104 may identify a plurality of historically vectorcardiogram images using the patient profile 128. As used in the current disclosure, a "historically vectorcardiogram image" is a vectorcardiogram image that was generated prior to a late (e.g., current) vectorcardiogram image 124. In some embodiments, historically vectorcardiogram images may include at least one diagnostic label 132 associated with them. Historically vectorcardiogram images may be used as a training data for a machine learning model or other algorithms. Historically vectorcardiogram images with known diagnostic labels may be used to train processor 104 on the patterns and associations between diagnostic features and specific cardiac conditions associated with the diagnostic labels 132. Historically vectorcardiogram images may be identified as a function of one or more of the patient's height, weight, BMI, gender, medical history, family medical history, and the like as identified by the patient profile 128.

With continued reference to FIG. 1, a processor 104 may identify a plurality of historically vectorcardiogram images using a lookup table. A "lookup table," for the purposes of this disclosure, is a data structure, such as without limitation an array of data, that maps input values to output values. A lookup table may be used to replace a runtime computation with an indexing operation or the like, such as an array indexing operation. A look-up table may be configured to pre-calculate and store data in static program storage, calculated as part of a program's initialization phase or even stored in hardware in application-specific platforms. Data within the lookup table may include historically vectorcardiogram images, diagnostic features, diagnostic labels. Data within the lookup table may be received from database 300. Lookup tables may also be used to identify a plurality of historically vectorcardiogram images by matching an input value to an output value by matching the input against a list of valid (or invalid) items in an array. In a non-limiting example, a historically vectorcardiogram images may include one or more identified diagnostic features and diagnostic labels. A lookup table may look up the patient profile 128 or diagnostic feature as an input and output a list of historically vectorcardiogram images. Processor 104 may be configured to "lookup" or input one or more of patient profile 128, diagnostic labels 132, diagnostic features, examples of historically vectorcardiogram images, and the like. Whereas the output of the lookup table may include a list of historically vectorcardiogram images tailored to the input value. Alternatively, or additionally, a query representing patient profile 108 may be submitted to the lookup table and/or a database, and an associated data fault identifier stored in a data record within the lookup table and/or database may be retrieved using the query.

With continued reference to FIG. 1, processor 104 may identify a diagnostic feature associated with the vectorcardiogram image 124. As used in the current disclosure, a "diagnostic feature" is a characteristic or component of information that provides diagnostically useful information. Processor 104 may identify diagnostic features by comparing vectorcardiogram image 124 to historically vectorcardiogram images. Historically vectorcardiogram images are discussed in greater detail herein below. In some cases, diagnostic features may be realized through a twostep process (1) recognition of features within vectorcardiogram image 124; and (2) identification of certain features diagnostically useful or otherwise correlated to heart conditions or activity. In some cases, recognition of features within vectorcardiogram image 124 may include a visualization of vectorcardiogram image 124. Exemplary visualizations of vectorcardiogram images are described in reference to FIGS. 7A-C and 8 below. In some cases, visualizations of vectorcardiogram images 124 may be processed for feature detection according to machine vision methods.

Still referring to FIG. 1, in some embodiments, processor 104 may receive as input visualizations of vectorcardiogram images 124 and output determinations about features and electrical activity of a heart. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, processor 104 may perform one or more transformations, for instance to orient a visualization (or an image or video) relative a desired coordinate system; exemplary transformations include without limitation homography transforms and affine transforms. Processor 104 may perform additional transformations, for example transformations that enhance contrast for feature detection (e.g., Gaussian blur or wavelet transformation).

Still referring to FIG. 1, processor 104 may receive vectorcardiogram image as input and output features within vectorcardiogram image 124. As an example, feature recognition or feature learning may use clustering algorithms such as K-means and particle swarm optimization. A k-means clustering algorithm receives vectorcardiogram image 124 and outputs a definite number of classified data entry clusters, features, wherein the data entry clusters each contain cluster data entries. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to identify clusters of closely related vectorcardiogram image 124, which may be provided with cardiac labels; this may, for instance, generate an initial set of cardiac labels from an initial set of vectorcardiogram image data, and may also, upon subsequent iterations, identify new clusters to be provided new cardiac labels, to which additional vectorcardiogram image data may be classified, or to which previously used vectorcardiogram image data may be reclassified.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids ci of centroids in set C. Unclassified data may be assigned to a cluster based on $\mathrm{argmin}_{ci \ni C} \mathrm{dist}(ci,x)^2$, where argmin includes argument of the minimum, ci includes a collection of centroids in a set C, and dist includes standard Euclidean distance. K-means clustering module may then recompute centroids by taking mean of all cluster data entries assigned to a centroid's cluster. This may be calculated based on $ci = 1/|Si|\Sigma xi \ni Si^{xi}$. K-means clustering algorithm may continue to repeat these calculations until a stopping criterion has been satisfied such as when cluster data entries do not change clusters, the sum of the distances have been minimized, and/or some maximum number of iterations has been reached.

Still referring to FIG. 1, k-means clustering algorithm may be configured to calculate a degree of similarity index value. A "degree of similarity index value" as used in this disclosure, includes a distance measurement indicating a measurement between each data entry cluster generated by k-means clustering algorithm and a selected vectorcardiogram image 124. Degree of similarity index value may indicate how close at least a portion of a vectorcardiogram image 124 is to being classified by k-means algorithm to a particular cluster. K-means clustering algorithm may evaluate the distances of vectorcardiogram images to the k-number of clusters output by k-means clustering algorithm. Short distances between a set of physiological data and a cluster may indicate a higher degree of similarity between the set of vectorcardiogram image data and a particular cluster. Longer distances between a set vectorcardiogram image data and a cluster may indicate a lower degree of similarity between a vectorcardiogram image set and a particular cluster.

With continued reference to FIG. 1, k-means clustering algorithm selects a classified data entry cluster as a function of the degree of similarity index value. In an embodiment, k-means clustering algorithm may select a classified data entry cluster with the smallest degree of similarity index value indicating a high degree of similarity between a vectorcardiogram image set and the data entry cluster. Alternatively or additionally k-means clustering algorithm may select a plurality of clusters having low degree of similarity index values to vectorcardiogram image, indicative of greater degrees of similarity. Degree of similarity index values may be compared to a threshold number indicating a minimal degree of relatedness suitable for inclusion of a set of vectorcardiogram image in a cluster, where degree of similarity indices a-n falling under the threshold number may be included as indicative of high degrees of relatedness. The above-described illustration of feature learning using k-means clustering is included for illustrative purposes only, and should not be construed as limiting potential implementation of feature learning algorithms; persons skilled in the art, upon reviewing the entirety of this disclosure, will be aware of various additional or alternative feature learning approaches that may be used consistently with this disclosure.

Processor 104 may analyze specific attributes such as loop shape, size, orientation, rotation, axis deviation, waveform characteristics, or spatial distribution of electrical vectors. The goal is to extract quantitative measurements or descriptors that capture the diagnostic information encoded in the vectorcardiogram image 124. Processor 104 may then identify the most informative and discriminative features among the extracted ones. This can be done using statistical analysis, information theory, or other feature selection techniques. The aim is to reduce the dimensionality of the feature space while retaining the most relevant diagnostic features. Processor 104 may then employ machine learning algorithms or pattern recognition techniques to classify the vectorcardiogram image 124 based on the extracted features. These algorithms can include decision trees, support vector machines, artificial neural networks, or deep learning models. In some cases, identifying significant features could include using a second vector-matching process, in which (1) features, or records that include candidate features, are vectorized; (2) a set of records are labeled as "clinically significant"; and (3) the two vector sets are compared using distance metrics (e.g. cosine similarity). Alternatively, users could label clinically significant events or additional information, such as text associated with an electrocardiogram, may be matched to labels, for example by using a language processing module. In some cases, labeled records' feature sets may be tabulated, and relative frequency and/or other statistics associated with the tabulated features could be used to select most important, e.g. diagnostically useful, features (threshold comparison, etc.). Further disclosure related to feature recognition, labelling, correlation, and classification may be found in SYSTEMS AND METHODS FOR EXPANDINF CLINICAL COHORTS FOR IMPROVED EFFICIACY OF SUPERVISED LEARNING, U.S. Provisional Patent Application No. 63/395,063, filed Aug. 4, 2022, the entirety of which is incorporated herein by reference.

With continued reference to FIG. 1, diagnostic features of the vectorcardiogram image 124 may include size, shape, rotation, and orientation of the vector loop as well as an output from any feature detection algorithm. In some cases, feature recognition may include one or more of frequency, phase changes, Fourier decomposition, and any signal process described in this disclosure. The vector loop represents the trajectory followed by the cardiac vector 120 during the cardiac cycle. Processor 104 may assess the vector loop's symmetry, regularity, and abnormalities, by identifying any variations in loop size, which may indicate changes in the magnitude of electrical vectors. Processor 104 may assess vector magnitude, vector angle, and/or other singular features in isolation, for example using machine learning processes and/or other analysis. In some cases, for example only vector magnitude change may be transformed to a waveform, analyzed using frequency analysis. Any abnormalities or changes in the loop can indicate cardiac abnormalities or altered electrical conduction. An additional example of a diagnostic feature may be when the vector loop has some sort of axis deviation. Axis deviation may refer to the deviation of the vector loop from expected axis. It may indicate a shift in the spatial orientation of the electrical vectors within the heart. Axis deviation can provide valuable diagnostic information, such as the presence of left ventricular hypertrophy or bundle branch blocks. Expected axis may include a typical axis, e.g., an average over a series of heartbeats (i.e., an average achieved during sinus rhythm). In some cases, expected axis may be compared to instances of cardiac conditions associated with an atypical vector loop axis (e.g., tachycardia, fibrillation, etc.) In some cases, monitoring of vector loop axis may be performed when monitoring for episodic cardiac rhythm disorders. In some cases, expected axis of a vector loop may be determined over a population of healthy electrocardiogram patterns, labeled by experts or any supervised/semi-supervised method described in this disclosure. In some cases, average vector loop axis may be determined for a similar cohort to patient in question. Diagnostic features may include the rotation of the vector loop, wherein the rotation of the vector loop may describe the change in orientation during different phases of the cardiac cycle. The rotation of the vector loop may reflect the sequential activation and propagation of electrical impulses within the heart. The direction and extent of loop rotation can provide insights into the timing and coordination of electrical events. A diagnostic feature may include the size of the vector loop, wherein the size of the vector loop represents the magnitude or strength of the electrical vectors generated by the heart. A larger loop indicates a greater magnitude of electrical activity, while a smaller loop suggests a weaker or altered electrical conduction. Changes in loop size can indicate changes in cardiac function. Diagnostic features may include waveform analysis. Within the vector loop, various waveforms may be observed, such as the P-wave, QRS complex, and T-wave. These waveforms represent the depolarization and repolarization of the atria and ventricles. Analyzing the position, orientation, and characteristics of these waveforms within the vector loop can provide information about the spatial distribution and sequence of electrical activity. In some cases, vector could be decomposed to one or more two-dimensional or other waveforms for ease of analysis. Additional reference points may be included in the vectorcardiogram image 124 to aid in interpretation. These points could indicate specific landmarks or time points within the cardiac cycle, such as the onset of ventricular activation (R-point) or the peak of the T-wave.

With continued reference to FIG. 1, processor 104 may identify diagnostic feature using a feature machine-learning model. As used in the current disclosure, a "feature machine machine-learning model" is a machine-learning model that is configured to identify one or more diagnostic features. Feature machine machine-learning model may be consistent with the machine-learning model described below in FIG. 2. Inputs to the feature machine machine-learning model may include an ECG signal 108, lead system, transformed coordinates, cardiac vector 120, vectorcardiogram image 124, historically vectorcardiogram image, examples of diagnostic feature, and the like. Outputs to the feature machine machine-learning model may include diagnostic feature tailored to the vectorcardiogram image 124. Feature training data may include a plurality of data entries containing a plurality of inputs that are correlated to a plurality of outputs for training a processor by a machine-learning process. In an embodiment, feature training data may include a plurality of historically vectorcardiogram image correlated to examples of diagnostic features. As described above, feature learning algorithms may include k-means clustering, particle swarm optimization, and the like. Identification of features may include identification of diagnostic features correlated to heart conditions of interest. Diagnostic features may be labeled as described above or by any other feature learning method known in the art.

Feature training data may be received from database 300. Feature training data may contain information about ECG signal 108, lead system, transformed coordinates, cardiac vector 120, vectorcardiogram image 124, historically vectorcardiogram image, examples of diagnostic feature, and the like. In an embodiment, feature training data may be iteratively updated as a function of the input and output results of past feature machine machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model.

With continued reference to FIG. 1, processor 104 may be configured to assign at least one diagnostic label 132 to the patient and/or patient profile 128 as a function of the vectorcardiogram image 124. As used in the current disclosure, a "diagnostic label" is a label used describe a specific condition, disorder, or illness that affects an individual's health or heart structure or function. A diagnostic label 132 may be associated any specific condition, disorder, or illness, specifically any conditions associated with the heart. In a non-limiting example, diagnostic labels 132 may be associated with conditions related to the cardiac health such as normal sinus rhythm, atrial fibrillation, myocardial infarction, ventricular tachycardia, bundle branch bloc, arrythmias, ischemic heart disease, heart enlargement, conduction abnormalities, cardiac ischemia, electrolyte imbalances, and the like. Processor 104 may assign a diagnostic label 128 to patient as function of the diagnostic features and the patient profile 128 of the vectorcardiogram image 124. Processor 104 may assign a diagnostic label 132 by comparing the current vectorcardiogram image 124 to the historically vectorcardiogram images. The comparison may include comparing the diagnostic features of the current vectorcardiogram image 124 to the historically vectorcardiogram images for similarities or differences. This may also be cross referenced with the patient profile 128, wherein the patient profile may provide additional context for the comparison. Processor 104 may employ pattern matching techniques to identify specific patterns or abnormalities within the vectorcardiogram image 124 to generate diagnostic label 132. This can involve comparing specific segments, intervals, or waveforms of the vectorcardiogram image 124 to detect similarities or differences. Cross-correlation, template matching, or dynamic time warping algorithms may be used for this purpose. Processor 104 may perform statistical analysis on various parameters derived from the vectorcardiogram image 124 to generate diagnostic label 132. This can involve calculating means, standard deviations, or other statistical measures for specific features or segments of the vectorcardiogram image 124. By comparing these statistical parameters, the computer can identify significant differences or similarities between the vectorcardiogram image 124. Diagnostic label 132 may be associated with one or more diagnostic features. This may mean that if the diagnostic features appear within the vectorcardiogram image 124 it may be likely that the patient has a given condition, disorder, or illness. In a non-limiting example, processor 104 assign the patient a diagnostic label 132 associated with a specific cardiac condition because the diagnostic features associated with a specific cardiac condition in the historically vectorcardiogram image align with the current diagnostic features of vectorcardiogram image 124.

With continued reference to FIG. 1, processor 104 may identify diagnostic feature using an assignment machine-learning model 136. As used in the current disclosure, an "assignment machine-learning model" is a machine-learning model that is configured to assign a diagnostic label 132. Assignment machine-learning model 136 may be consistent with the machine-learning model described below in FIG. 2. Inputs to the assignment machine-learning model 136 may include an ECG signal 108, lead system, transformation matrix 116, transformed coordinates, cardiac vector 120, vectorcardiogram image 124, historically vectorcardiogram image, diagnostic feature, examples of diagnostic label 132, and the like. Outputs to the assignment machine-learning model 136 may include assigning a diagnostic label 132 tailored to the vectorcardiogram image 124. Assignment training data may include a plurality of data entries containing a plurality of inputs that are correlated to a plurality of outputs for training a processor by a machine-learning process. In an embodiment, assignment training data may include a plurality of historically vectorcardiogram image correlated to examples of vectorcardiogram image 124. In another embodiment, assignment training data may include a plurality of historically vectorcardiogram image which includes a plurality of diagnostic features correlated to examples of vectorcardiogram image 124. Assignment training data may be received from database 300. Assignment training data may contain information about ECG signal 108, lead system, transformation matrix 116, transformed coordinates, cardiac vector 120, vectorcardiogram image 124, historically vectorcardiogram image, diagnostic feature, examples of diagnostic label 132, and the like. In an embodiment, assignment training data may be iteratively updated as a function of the input and output results of past assignment machine-learning model 136 or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model.

With continued reference to FIG. 1, processor 104 may compare a vectorcardiogram image 124 to a historically vectorcardiogram image using a comparison fuzzy inference. As used in the current disclosure, a "comparison fuzzy inference" is a method that interprets the values in the input vector (i.e., vectorcardiogram image 124 and historically vectorcardiogram image.) and, based on a set of rules, assigns values to the output vector. A set of fuzzy rules may include a collection of linguistic variables that describe how the system should make a decision regarding classifying an input or controlling an output. Fuzzy inference rules operate on fuzzy sets and provide a framework for mapping input variables to output variables through linguistic rules. Fuzzy inference rules may operate using linguistic variables, which represent imprecise or vague concepts rather than precise numerical values. Linguistic variables are defined by membership functions, which describe the degree of membership or truth for different linguistic terms or categories. In a non-limiting example, a linguistic variable associated with diagnostic label 132 may have linguistic terms like "Myocardial Infarction," "Ventricular Tachycardia," "heart enlargement," and the like each with its corresponding membership function. A fuzzy inference rule typically follows a conditional "IF-THEN" structure. It consists of an antecedent (IF part) and a consequent (THEN part). The antecedent specifies the conditions or criteria based on which the rule will be applied, and the consequent determines the output or conclusion of the rule. In an embodiment, an assignment of a diagnostic label 132 may be determined by a comparison of the degree of match between a first fuzzy set and a second fuzzy set, and/or single values therein with each other or with either set, which is sufficient for purposes of the matching process.

Still referring to FIG. 1, an assignment of a diagnostic label 132 may be determined as a function of the intersection between two fuzzy sets, wherein each fuzzy set may be representative of a vectorcardiogram image 124 and a historically vectorcardiogram image, respectively. Comparing the vectorcardiogram image 124 and a historically vectorcardiogram image may include utilizing a fuzzy set inference system as described herein below, or any scoring methods as described throughout this disclosure. For example, without limitation, processor 104 may use a fuzzy logic model to determine assign one or more diagnostic label 132 as a function of fuzzy set comparison techniques as described in this disclosure. In some embodiments, each piece of information associated with a vectorcardiogram image 124 may be compared to a historically vectorcardiogram image, wherein a diagnostic label 132 may be represented using a linguistic variable on a range of potential numerical values, where values for the linguistic variable may be represented as fuzzy sets on that range; a "good" or "ideal" fuzzy set may correspond to a range of values that can be characterized as ideal, while other fuzzy sets may correspond to ranges that can be characterized as mediocre, bad, or other less-than-ideal ranges and/or values. In embodiments, these variables may be used to compare a vectorcardiogram image 124 and a historically vectorcardiogram image to assign a diagnostic label 132 specific to the vectorcardiogram image 124. A fuzzy inferencing system may combine such linguistic variable values according to one or more fuzzy inferencing rules, including any type of fuzzy inferencing system and/or rules as described in this disclosure, to determine a degree of membership in one or more output linguistic variables having values representing ideal overall performance, mediocre or middling overall performance, and/or low or poor overall performance; such mappings may, in turn, be "defuzzified" as described in further detail below to provide an overall output and/or assessment.

Still referring to FIG. 1, the processor may be configured to generate a machine-learning model, such as assignment machine-learning model, using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)=P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Still referring to FIG. 1, processor 104 may be configured to generate a machine-learning model, such as assignment machine-learning model, using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm $l=\sqrt{\Sigma_{i=0}^{n} a_i^2}$, where $a_i$, is attribute number experience of the vector. Scaling and/or normalization may function to make vector comparison independent of absolute quantities of attributes, while preserving any dependency on the similarity of attributes; this may, for instance, be advantageous where cases represented in training data are represented by different quantities of samples, which may result in proportionally equivalent vectors with divergent values.

With continued reference to FIG. 1, processor 104 may generate a confidence score as a function of the assignment of the diagnostic label 132. As used in the current disclosure, a "confidence score" is quantitative measurement of the accuracy of the assignment of the diagnostic label 132. Accuracy of the assignment of the diagnostic label 132 may refer to likelihood of an accurate diagnosis of the condition, disease, or issue experienced by the patient. A processor 104 may generate a confidence score for each diagnostic label 132 assigned to the vectorcardiogram image 124. Processor 104 may calculate a confidence score based on the similarity or dissimilarity between the two diagnostic labels 132 based on the diagnostic features that have been extracted from a vectorcardiogram image 124. Various similarity metrics can be employed, such as Euclidean distance, cosine similarity, Jaccard similarity, or any other appropriate measure for the type of data being compared. Processor 104 may use the calculated similarity or dissimilarity values to generate a confidence score. This score may represent the level of confidence or certainty in the accuracy in the assignment of a diagnostic label 132. The score can be computed based on statistical methods, probability models, or decision rules based on the patient profile 128 and the extracted diagnostic features. A confidence score may be used to normalize one or more assignments of the diagnostic label 132 onto a comparable scale. This step is important to eliminate any bias introduced by different qualities the vectorcardiogram image 124. Normalization techniques can include min-max scaling, z-score normalization, or logarithmic transformation. In an embodiment, if the assignment of the diagnostic label 132 is likely to be accurate then the confidence score may be high, conversely assignment of the diagnostic label 132 is likely inaccurate then the confidence score may be low. A confidence score may be expressed as a numerical score, a linguistic value, alphanumeric score, or an alphabetical score. Confidence score may be represented as a score used to reflect the level of accuracy of the assigned of the diagnostic label 132. A non-limiting example, of a numerical score, may include a scale from 1-10, 1-100, 1-1000, and the like, wherein a rating of 1 may represent an inaccurate assignment of the diagnostic label 132, whereas a rating of 10 may represent an accurate assignment of the diagnostic label 132. In another non-limiting example, linguistic values may include, "Highly Accurate," "Moderately Accurate," "Moderately Inaccurate," "Highly Inaccurate," and the like. In some embodiments, linguistic values may correspond to a numerical score range. For example, assignment of the diagnostic label 132 that receives a score between 50-75, on a scale from 1-100, may be considered "Moderately Accurate."

With continued reference to FIG. 1, processor 104 may generate the confidence score using a score machine-learning model. As used in the current disclosure, an "score machine-learning model" is a machine-learning model that is configured to generate a confidence score. The score machine-learning model may be consistent with the machine-learning model described below in FIG. 2. Inputs to the score machine-learning model may include ECG signal 108, lead system, transformed coordinates, cardiac vector 120, vectorcardiogram image 124, historically vectorcardiogram image, diagnostic feature, diagnostic label 132, examples of confidence scores, and the like. Outputs to the score machine-learning model may include a confidence score tailored to one or more diagnostic labels 132. Score training data may include a plurality of data entries containing a plurality of inputs that are correlated to a plurality of outputs for training a processor by a machine-learning process. In an embodiment, score training data may include a plurality of diagnostic label 132 correlated to examples of confidence scores. Examples of confidence scores may include historical confidence scores that have been generated from previous iterations of score machine learning model or apparatus 100. Score training data may be received from database 300. Score training data may contain information regarding ECG signal 108, lead system, transformed coordinates, cardiac vector 120, vectorcardiogram image 124, historically vectorcardiogram image, diagnostic feature, diagnostic label 132, examples of confidence scores, and the like. In an embodiment, a score machine-learning model may be iteratively updated with the input and output results of past score machine-learning models. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, processor 104 may generate a diagnostic report based on the assignment of one or more diagnostic labels 132. As used in the current disclosure, a "diagnostic report" is a summary of analysis performed on the vectorcardiogram image 124 and resulting assignment of one or more diagnostic labels 132. A diagnostic report may detail a plurality of information associated with patient profile 128. A diagnostic report describes essential patient information, such as the patient's name, age, sex, and any relevant medical identifiers. This information ensures proper identification of the patient and helps to associate the diagnostic findings with the correct individual. The diagnostic report may include the date and time of the recording of the vectorcardiogram image 124, the signal or electrode configuration employed, and any specific instructions or conditions during the recording process. These details provide context for the subsequent analysis and interpretation. The report may include technical findings related to the quality and validity of the vectorcardiogram image 124. This can involve observations or notes about signal quality, the presence of artifacts or noise, or any technical issues that may have influenced the analysis. These findings help to assess the reliability of the diagnostic conclusions. The report may include the diagnostic features from the vectorcardiogram image 124, along with other features such as loops, loop orientation, loop shape, QRS complex characteristics, ST-segment abnormalities, and any other relevant parameters derived from the VCG data. The report may provide numerical values, graphical representations, or visual illustrations of these features to aid in understanding. Based on the analysis of the diagnostic features, the report may include diagnostic conclusions associated with the diagnostic labels 132. It identifies any abnormalities or specific cardiac conditions present in the vectorcardiogram image 124. The diagnostic conclusions can be binary (normal vs. abnormal) or multiclass labels representing different cardiac conditions. Each conclusion is supported by the analysis of the extracted features and may include a confidence level or severity assessment.

Still referring to FIG. 1, processor 104 may be configured to display the diagnostic label 132 using a display device 140. As used in the current disclosure, a "display device" is a device that is used to display content. A display device 140 may include a user interface. A "user interface," as used herein, is a means by which a user and a computer system interact; for example, through the use of input devices and software. A user interface may include a graphical user interface (GUI), command line interface (CLI), menu-driven user interface, touch user interface, voice user interface (VUI), form-based user interface, any combination thereof, and the like. A user interface may include a smartphone, smart tablet, desktop, or laptop operated by the user. In an embodiment, the user interface may include a graphical user interface. A "graphical user interface (GUI)," as used herein, is a graphical form of user interface that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like.

Figure 2:
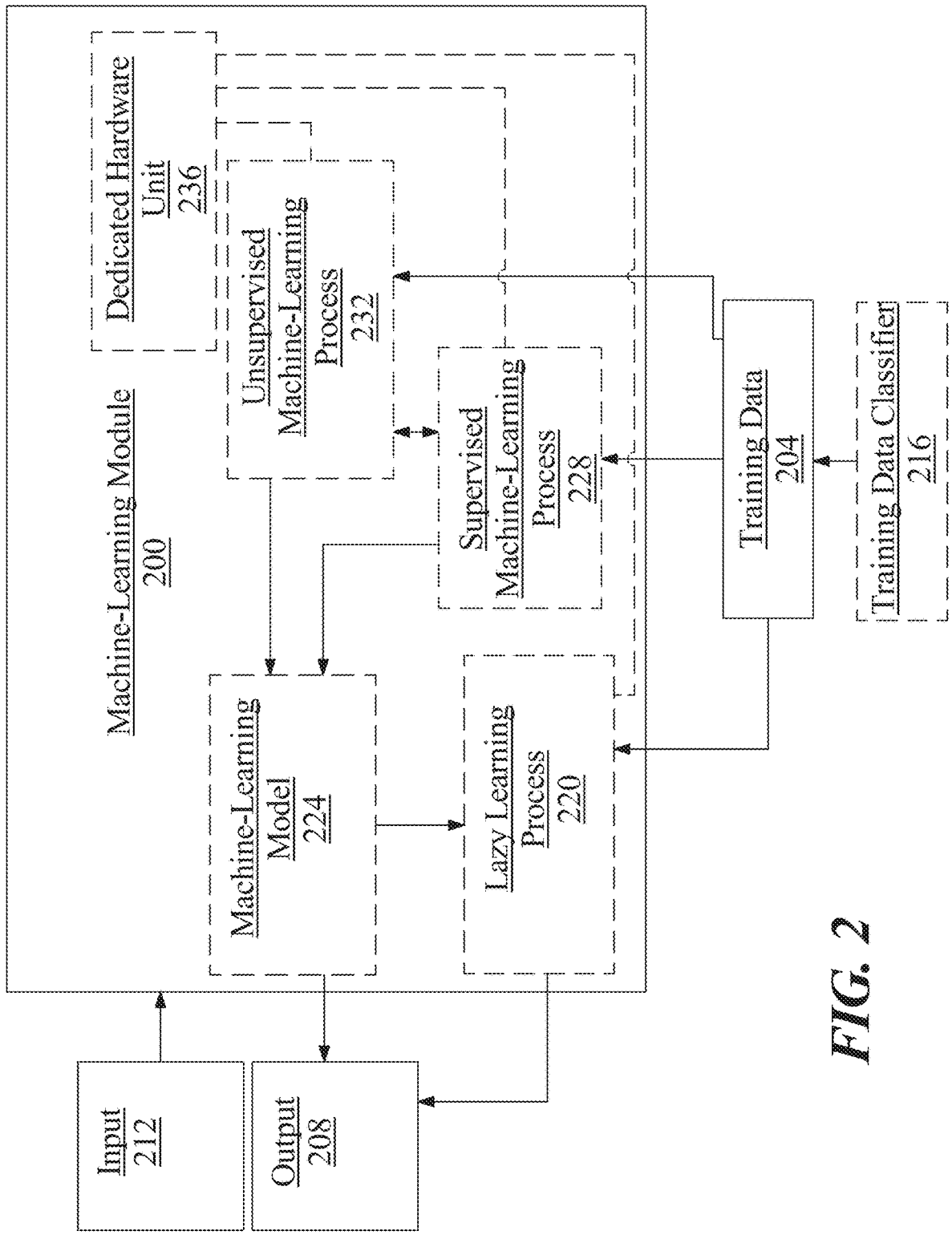
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With further reference to FIG. 2, training examples for use as training data may be selected from a population of potential examples according to cohorts relevant to an analytical problem to be solved, a classification task, or the like. Alternatively, or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, patient data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively, or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively, or additionally, one or more training examples may identify as having poor quality data, where "poor quality" is defined as having a signal to noise ratio below a threshold value.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively, or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean upside-effects of compression.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include historically vectorcardiogram images as described above as inputs, at least one diagnostic label 132 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively, or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized, or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 232. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 232 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 232 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 232 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
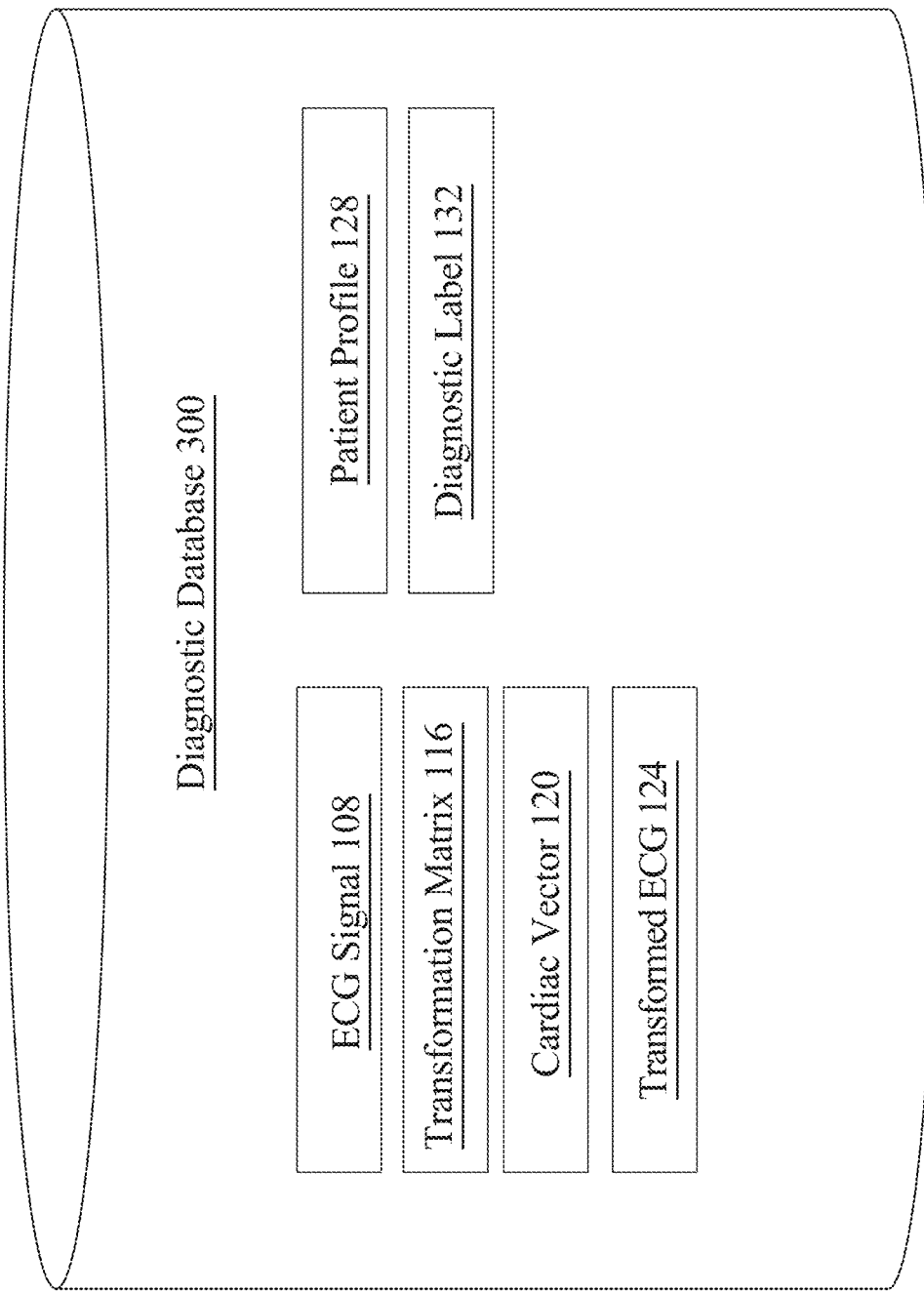
FIG. 3 is a block diagram of an exemplary embodiment of a diagnostic database.

Now referring to FIG. 3, an exemplary diagnostic database 300 is illustrated by way of block diagram. In an embodiment, any past or present versions of any data disclosed herein may be stored within the diagnostic database 300 including but not limited to: ECG signal 108, lead system, transformed coordinates, cardiac vector 120, vectorcardiogram image 124, historically vectorcardiogram image, diagnostic feature, diagnostic label 132, confidence scores, diagnostic reports, and the like. Processor 104 may be communicatively connected with diagnostic database 300. For example, in some cases, database 300 may be local to processor 104. Alternatively, or additionally, in some cases, database 300 may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connects directly, dynamically, and non-hierarchically to as many other computing devices as possible. A "network topology" as used in this disclosure is an arrangement of elements of a communication network. Diagnostic database 300 may be implemented, without limitation, as a relational database, a key-value retrieval database such as a NOSQL database, or any other format or structure for use as a database that a person skilled in the art would recognize as suitable upon review of the entirety of this disclosure. Diagnostic database 300 may alternatively or additionally be implemented using a distributed data storage protocol and/or data structure, such as a distributed hash table or the like. Diagnostic database 300 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Figure 4:
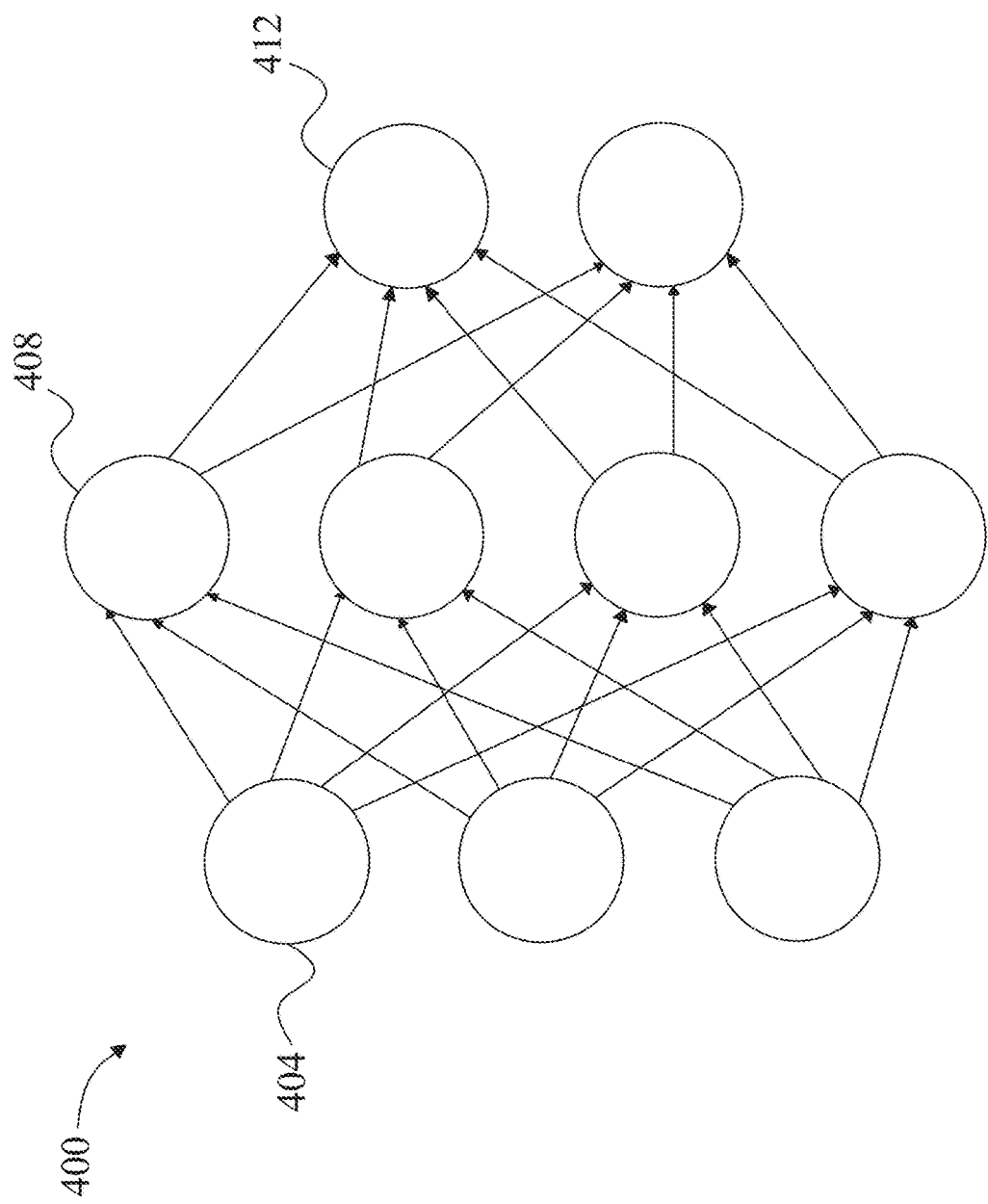
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
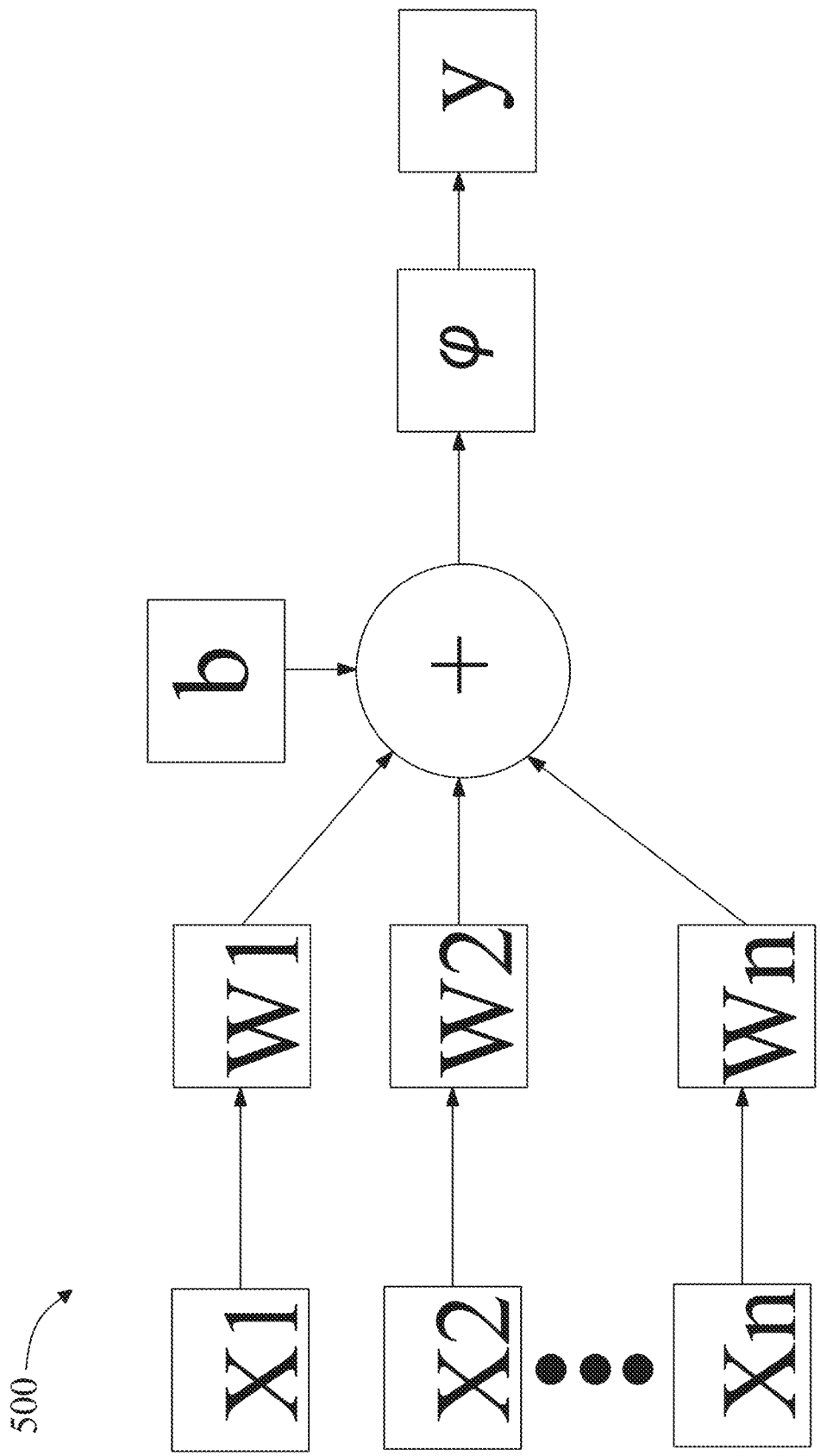
FIG. 5 is a diagram of an exemplary embodiment of a node of a neural network.

Referring now to FIG. 5, an exemplary embodiment of a node of a neural network is illustrated. A node may include, without limitation, a plurality of inputs x, that may receive numerical values from inputs to a neural network containing the node and/or from other nodes. Node may perform a weighted sum of inputs using weights w', that are multiplied by respective inputs x1. Additionally, or alternatively, a bias b may be added to the weighted sum of the inputs such that an offset is added to each unit in the neural network layer that is independent of the input to the layer. The weighted sum may then be input into a function o, which may generate one or more outputs y. Weight w', applied to an input x, may indicate whether the input is "excitatory," indicating that it has strong influence on the one or more outputs y, for instance by the corresponding weight having a large numerical value, and/or an "inhibitory," indicating it has a weak effect influence on the one more inputs y, for instance by the corresponding weight having a small numerical value. The values of weights w', may be determined by training a neural network using training data, which may be performed using any suitable process as described above.

Figure 6:
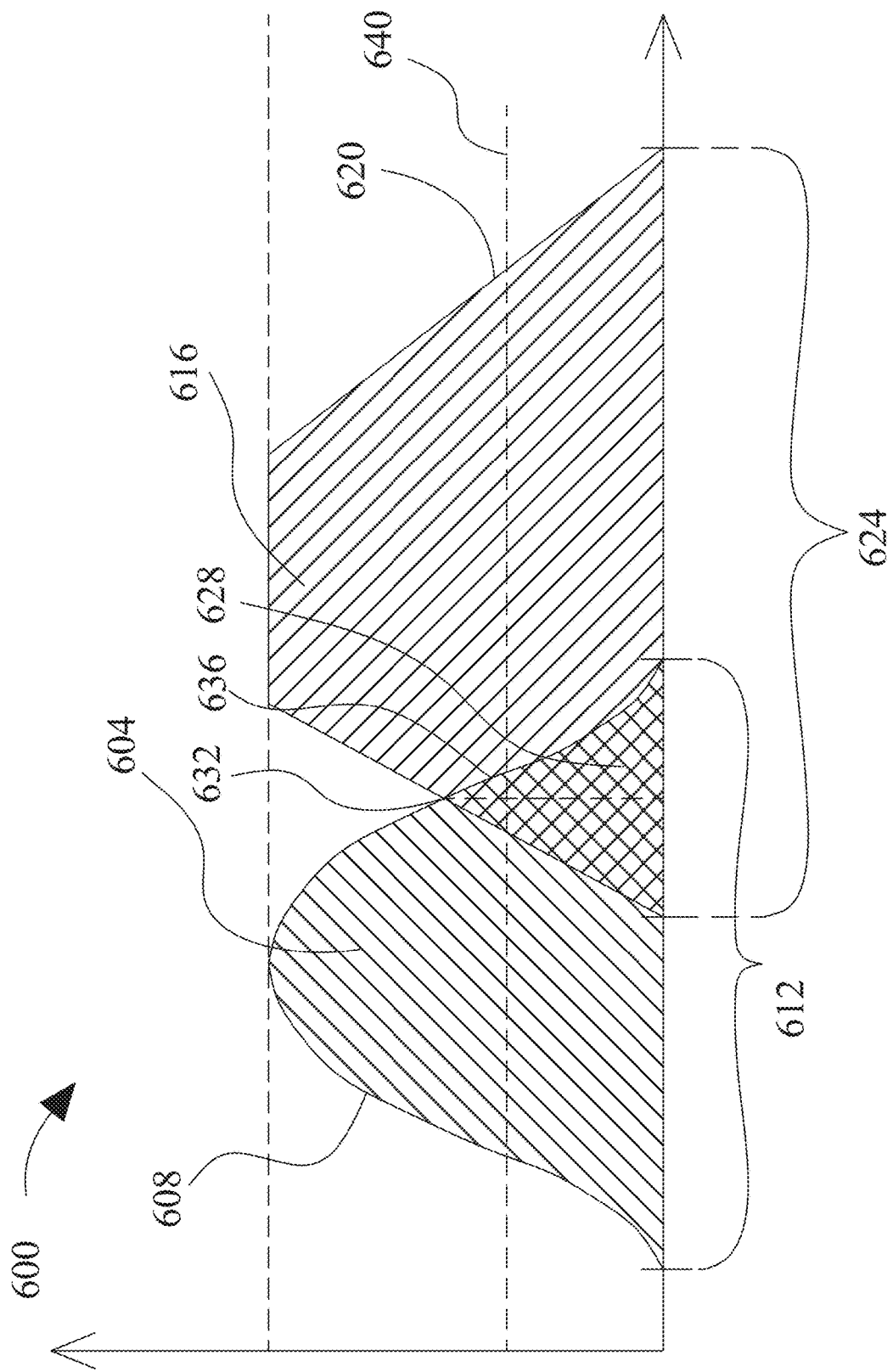
FIG. 6 is an illustration of an exemplary embodiment of fuzzy set comparison.

Now referring to FIG. 6, an exemplary embodiment of fuzzy set comparison 600 is illustrated. In a non-limiting embodiment, the fuzzy set comparison. In a non-limiting embodiment, fuzzy set comparison 600 may be consistent with fuzzy set comparison in FIG. 1. In another non-limiting the fuzzy set comparison 600 may be consistent with the name/version matching as described herein. For example, and without limitation, the parameters, weights, and/or coefficients of the membership functions may be tuned using any machine-learning methods for the name/version matching as described herein. In another non-limiting embodiment, the fuzzy set may represent a vectorcardiogram image 124 and historically vectorcardiogram image from FIG. 1.

Alternatively, or additionally, and still referring to FIG. 6, fuzzy set comparison 600 may be generated as a function of determining data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 6, inference engine may be implemented according to input a plurality of cardiac vectors 120 and/or vectorcardiogram images 124 and a plurality of historically vectorcardiogram images. For instance, an acceptance variable may represent a first measurable value pertaining to the classification of a plurality of vectorcardiogram image 124 to an historically vectorcardiogram image. Continuing the example, an output variable may represent at least one diagnostic label 132. In an embodiment, a plurality of vectorcardiogram image 124 and/or an historically vectorcardiogram image may be represented by their own fuzzy set. In other embodiments, an evaluation factor may be represented as a function of the intersection two fuzzy sets as shown in FIG. 6, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T (T(a, b), c)), and the requirement that the number 1 acts as an identity element. Combinations of rules ("and" or "or" combination of rule membership determinations) may be performed using any T-conorm, as represented by an inverted T symbol or "⊥," such as max(a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤ c and b≤d, associativity: ⊥(a, ⊥(b, c))=⊥(⊥(a, b), c), and identity element of 0. Alternatively, or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively, or additionally, output rules may be replaced with functions according to the Takagi-Sugeno-King (TSK) fuzzy model.

A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x,a,b,c,d)=\max(\min(x-a/b-,1,d-x/d-c),0)$$

a sigmoidal function may be defined as:

$$y(x,a,c)=1/1-e^{-a(x-c)}$$

a Gaussian membership function may be defined as:

$$y(x,c,\sigma)=e^{-1/2(x-c/\sigma)^2}$$

and a bell membership function may be defined as:

$$y(x,a,b,c,)=[1+|x-c/a|^{2b}]^{-1}$$

Persons skilled in the art, upon reviewing the entirety of this disclosure, will be aware of various alternative or additional membership functions that may be used consistently with this disclosure.

First fuzzy set 604 may represent any value or combination of values as described above, including any a plurality of vectorcardiogram image 124 and historically vectorcardiogram image. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 636 that overlaps, first membership function 608 and second membership function 620 may intersect at a point 632 representing a probability, as defined on probability interval, of a match between first fuzzy set 604 and second fuzzy set 616. Alternatively, or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, the assignment of at least one diagnostic label 132 may indicate a sufficient degree of overlap with fuzzy set representing a plurality of vectorcardiogram image 124 and an historically vectorcardiogram image for combination to occur as described above. Each threshold may be established by one or more user inputs. Alternatively, or additionally, each threshold may be tuned by a machine-learning process and/or statistical process, for instance and without limitation as described in further detail below.

In an embodiment, a degree of match between fuzzy sets may be used to rank one resource against another. For instance, if both a plurality of vectorcardiogram image 124 and a historically vectorcardiogram image have fuzzy sets, at least one diagnostic label 132 may be assigned by having a degree of overlap exceeding a predictive threshold, processor 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Figure 7A:
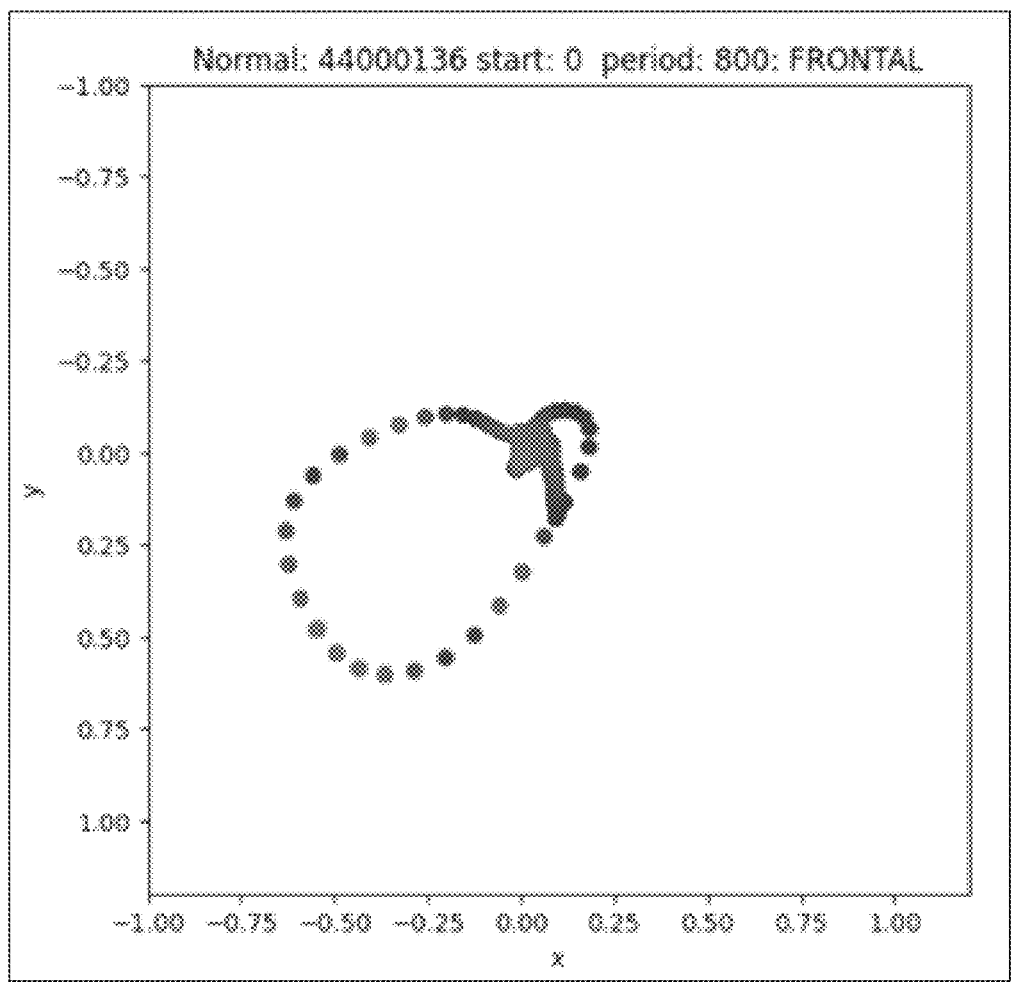
FIG. 7A is an illustration of an exemplary visualization of transformed ECG data.
Figure 7B:
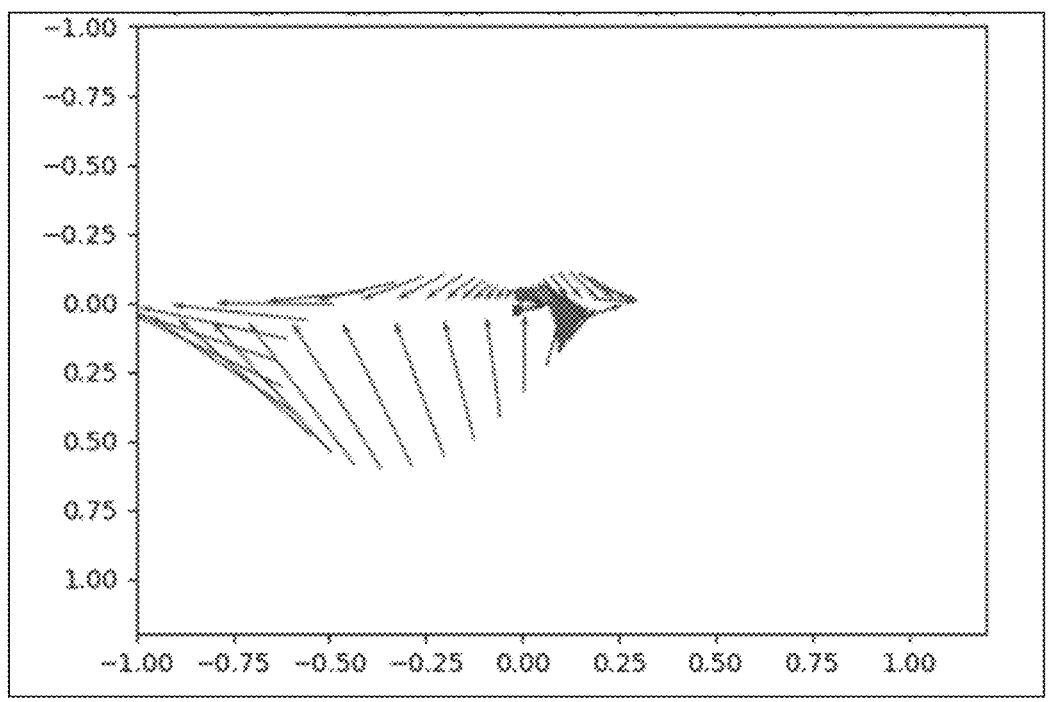
FIG. 7B is an illustration of another exemplary visualization of transformed ECG data.
Figure 7C:
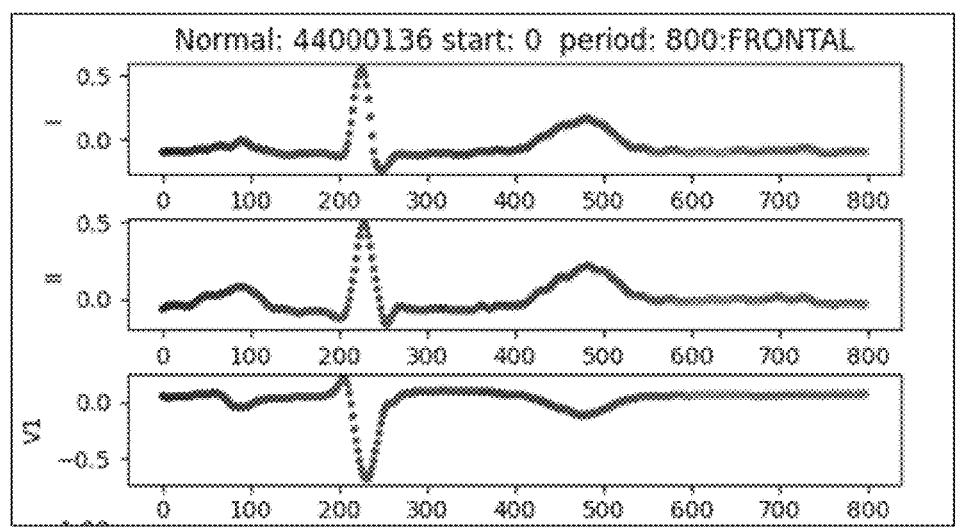
FIG. 7C is an illustration of yet another exemplary visualization of transformed ECG data.

Referring to FIGS. 7A-C, an exemplary embodiment of visualization of transformed ECGs is shown, for three overlapping time slices. In some cases, input ECGs may be a multi-lead ECG, for example a set of 12 leads; alternatively input ECG may include a subset of lead signals, e.g., a single lead ECG. An exemplary input ECG may include 5000 samples (e.g., 500 Hz sampling for 10 seconds) of 8 leads (5000×8). Input ECG may be transformed by an appropriately dimensioned matrix. For instance, an exemplary 5000-sample 8-lead (5000×8) input ECG may be transformed by a matrix of dimension 8×3 yielding a 5000×3 matrix. Generally, there is no constraint on transformation used. However, transformed vectors advantageous for visualization and further processing (e.g., feature detection) may be smooth along time axis and representative of key characteristics that aid in normal and disease fear true detection. In some cases, there is no constraint on reduction of dimension (i.e., size) of ECG data (e.g., number of leads), while preserving time axis during transformation. In some cases, transformation to an output ECG of two or three dimensions facilitates visual interpretation.

With continued reference to FIGS. 7A-C, transformed ECG may be shown. Visualization of transformed ECG may be presented by way of vector projections. For instance, vector projections of transformed ECG may be rendered in certain planes. FIGS. 7A-B illustrate a vector projection of transformed ECG in an orthogonal plane. In some cases, orthogonal plane may include any plane described in this disclosure, for example without limitation sagittal, transverse, and frontal.

Figure 8:
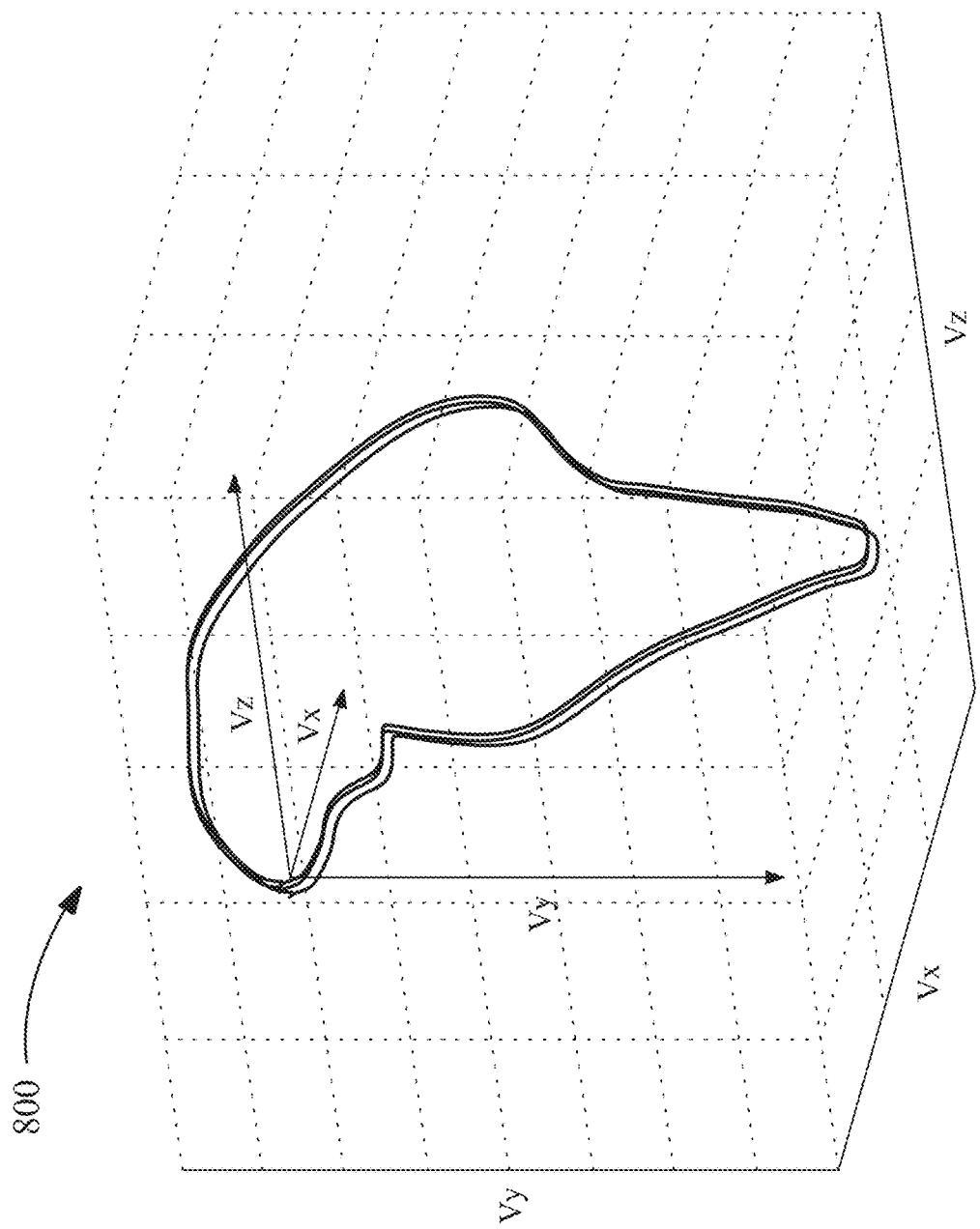
FIG. 8 is an illustration of an exemplary embodiment of vectorcardiogram image.

In FIG. 7A, each vector is shown rendered at a head position of the vector from an origin. In some cases, this rendering is similar to rendering all vectors positioned at origin. Head position rendering, in some instances, benefits human interpretation. Alternatively or additionally, head of vectors may be plotted alone with each corresponding vector rooted at origin. In FIG. 7B, each vector is shown rendered as a vector field, showing both magnitude and direction. Referring to FIGS. 7A-B, in some cases, visualized vectors might be shown terminating at vector loop, describing location of loop points. Alternatively or additionally, as shown in FIG. 8 below, origin of vector may be located at vector loop, suggesting the vectors describe a tangent envelope to the loop (e.g., velocity vectors).

Referring again to FIGS. 7A-C, visualizations for a specific projection may be rendered contiguous across time slices, having characteristics that are easily interpretable compared to corresponding ECG rendition. In some cases, renditions of contiguous time slices may be transformed into a video. Evolution of spatial representation shape of each time slice over time may reduce cognitive overload of feature extraction by humans and improve detectability of anomalies that are spread across both a single lead and multiple leads collectively over time.

FIG. 7C illustrates two dimensional representations of each dimension of a three-dimensional transformed ECG, with amplitude shown along a horizontal axis and time shown along a vertical axis. Visualizations according to that shown in FIG. 7C may show transformed ECG in sagittal, transverse, and frontal planes. Visualizations according to that shown in FIG. 7C may show transformed ECG over one or more heart cycles.

Referring again to FIGS. 7A-C, in some cases, visualizations may enable machine learning processes that use transformed ECGs and/or visualizations of transformed ECGs as inputs. Machine learning processes may include any machine learning process described in this disclosure. Exemplary machine learning process may include feature detectors, such as for scale invariant feature transform (SIFT), Canny edge detection, Shi Tomasi corner detection, and the like. In some cases. For example, in some embodiments visualization of transformed ECGs, like those shown in FIGS. 7A-C, may be input to image classifiers (e.g., supervised training or self-supervised learning), with or without an intervening feature detection step. In some cases, visualizations of transformed ECGs may be used as input to a machine learning processes paired with corresponding text.

Referring now to FIG. 8, is another illustration of an exemplary embodiment of vectorcardiogram image. The display device 140 may display the vectorcardiogram image 124 in a graphical format to facilitate visual comparison. In some cases, the vectorcardiogram images 124 can be overlaid on top of each other or displayed side by side for visual inspection and assessment of similarities or differences. Graphical representations, such as vector loops or waveform plots, can be used to aid in the comparison. In some cases, the display device 140 may display the vectorcardiogram image 124 in an annotated format along with diagnostic features and diagnostic labels 132. The vectorcardiogram image 124 provides valuable insights into the cardiac vector's 120 magnitude and direction during the cardiac cycle. In a vectorcardiogram image 124, several diagnostic features can be identified. The loop shape and size are indicative of the overall cardiac performance. Axis deviation, represented by the angle of the loop, can suggest abnormalities such as left ventricular hypertrophy or right ventricular strain. Loop rotation can reveal bundle branch blocks or ventricular tachycardia. The spatial distribution of electrical vectors helps assess chamber enlargement or myocardial infarction location. Each of these diagnostic features may be associated with one or more diagnostic labels 132. Diagnostic labels 132 associated with the vectorcardiogram image 124 may include normal sinus rhythm, atrial fibrillation, myocardial ischemia, ventricular hypertrophy, and bundle branch blocks. Analyzing diagnostic features and diagnostic labels 132 in a vectorcardiogram image 124 aids in diagnosing various cardiac conditions and guiding appropriate treatment strategies.

Figure 9:
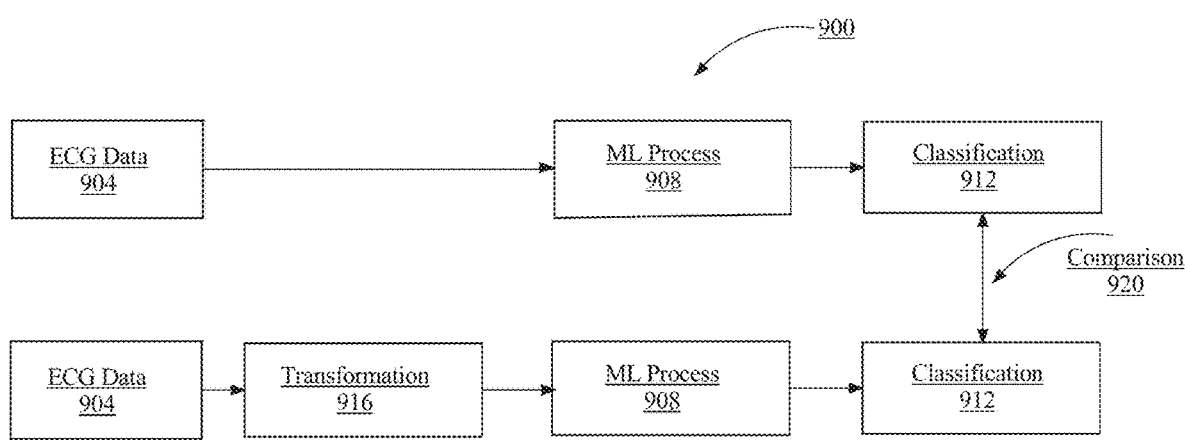
FIG. 9 is a block diagram of an exemplary method for comparing diagnostic processes.

Referring now to FIG. 9, a block diagram represents an exemplary system 900 for comparing usefulness of ECG transformation in classification. System 900 may receive ECG data 904. ECG data 904 may include 12-lead ECGs. System 900 may perform machine learning processes 908 and classification 912 on ECG data 904. Machine learning processes 908 and classification 912 may include any machine learning processes, models, classifiers, and the like described in this disclosure. System 900 may additionally transform 916 ECG data. For instances and without limitation, system 900 may transform 916 ECG data into a vectorcardiogram. System 900 may use comparable machine learning processes 908 and classify 912 transformed ECG data. For instance, system may use a transformer model to classify the resultant vector representation by heart condition. System 900 may compare 920 classification 912 with raw ECG data and transformed data 916. In some cases, transformation 916 of ECG data enables improved classification.

Figure 10:
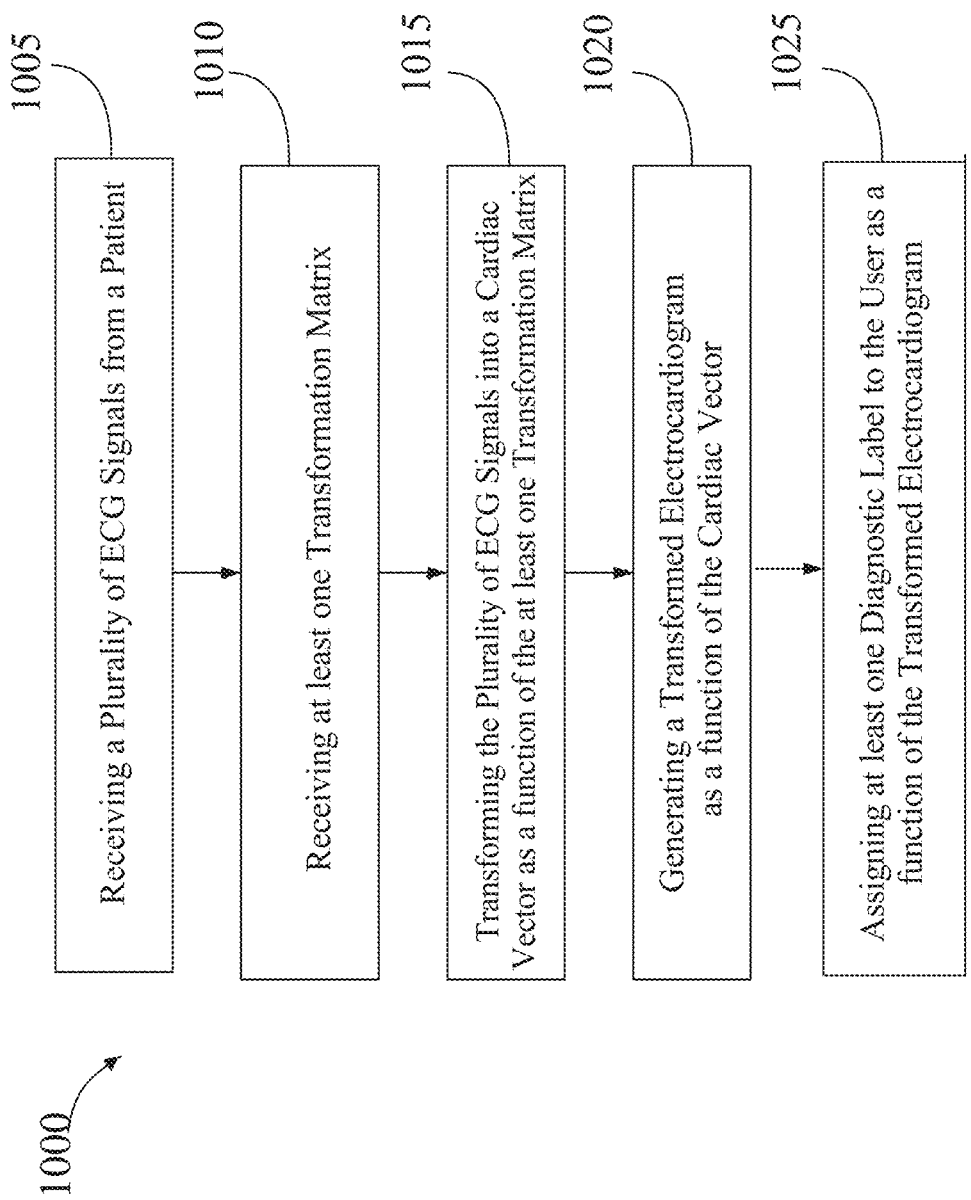
FIG. 10 is a flow diagram of an exemplary system for the improvement of electrocardiogram visualization.

Referring now to FIG. 10, a flow diagram of an exemplary method 1000 for the improvement of electrocardiogram visualization is illustrated. At step 1005, method 1000 includes receiving, using at least a processor, a plurality of electrocardiogram signals from a user, wherein each electrocardiogram signal of the plurality of electrocardiogram signals are generated using at least one sensor of a plurality of sensors attached to the user. This may be implemented as described and with reference to FIGS. 1-9.

Still referring to FIG. 10, at step 1010, method 1000 includes receiving, using the at least a processor, at least one transformation matrix. This may be implemented as described and with reference to FIGS. 1-9.

Still referring to FIG. 10, at step 1015, method 1000 includes transforming, using the at least a processor, the plurality of electrocardiogram signals into a cardiac vector as a function of the at least one transformation matrix. This may be implemented as described and with reference to FIGS. 1-9. In some embodiments, the method may include sorting, using the at least a processor, using each electrocardiogram signal of the plurality of electrocardiogram signals into at least one lead system. The at least one lead system may include a first group.

Still referring to FIG. 10, at step 1020, method 1000 includes generating, using the at least a processor, a vectorcardiogram image as a function of the cardiac vector. This may be implemented as described and with reference to FIGS. 1-9.

Still referring to FIG. 10, at step 1025, method 1000 includes assigning, using the at least a processor, at least one diagnostic label to the patient as a function of the vectorcardiogram image. This may be implemented as described and with reference to FIGS. 1-9. In some embodiments, the method may include generating, using the at least a processor, a confidence score as a function of the assignment of the at least one diagnostic label. In other embodiments, the method may include generating, using the at least a processor, a diagnostic report as a function of the at least one diagnostic label and the vectorcardiogram image. In some cases, assigning the at least one diagnostic label to the patient includes identifying a plurality of historically vectorcardiogram images as a function of the patient profile and assigning the at least one diagnostic label as a function of a comparison between the transformed cardiogram and the plurality of historically vectorcardiogram images. The method may include identifying, using the at least a processor, a diagnostic feature as a function of the vectorcardiogram image and a plurality of historically vectorcardiogram images. In some embodiments, assigning the at least one diagnostic label comprises assigning the at least one diagnostic label using an assignment machine-learning model. Wherein assigning the at least one diagnostic label using the assignment machine-learning model may include training the assignment machine-learning model using assignment training data, wherein the assignment training data contains a plurality of data entries containing the vectorcardiogram image and the patient profile as inputs correlated to the at least one diagnostic label as an output.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
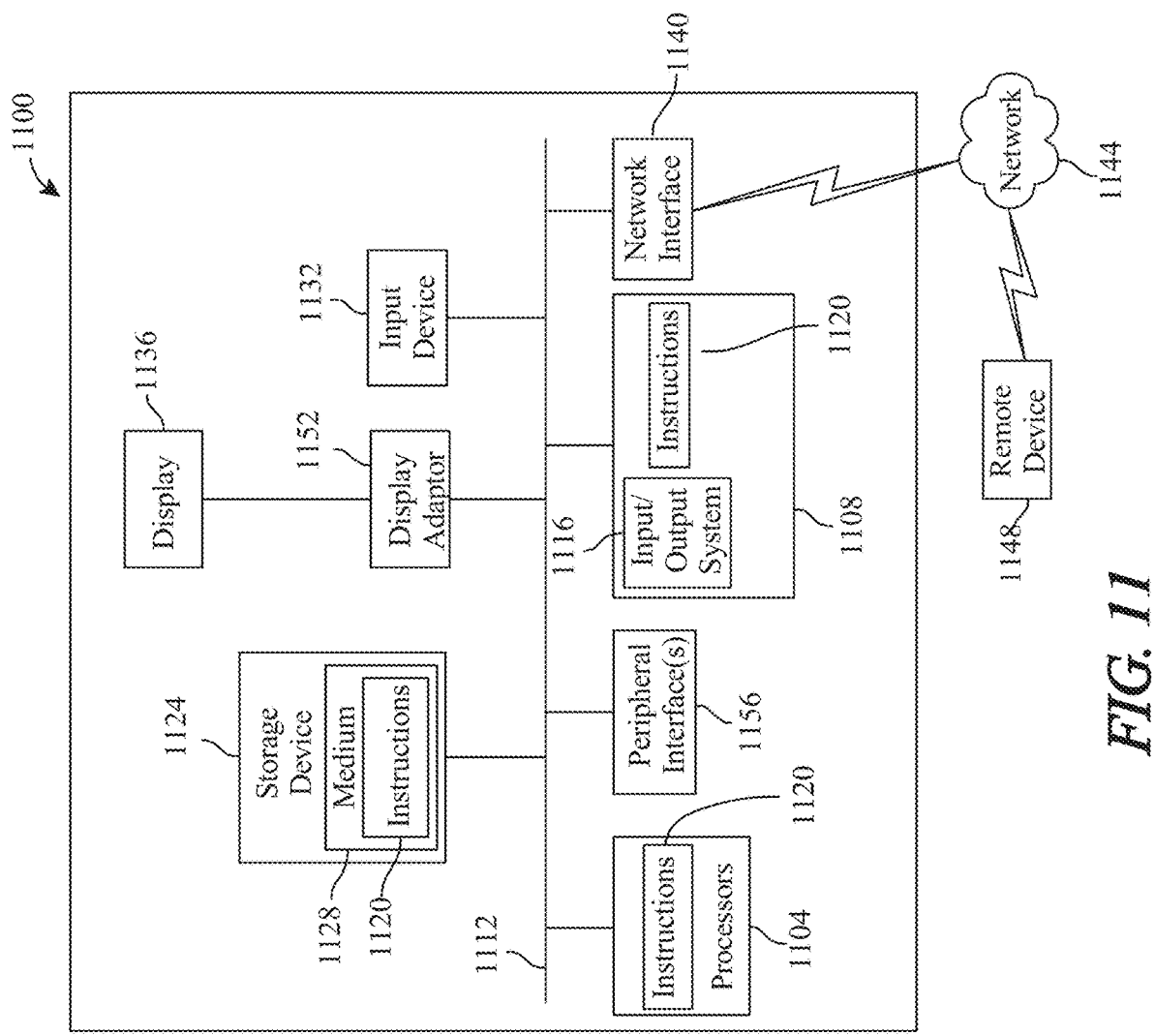
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Processor 1104 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1104 may be organized according to Von Neumann and/or Harvard architecture as a non-limiting example. Processor 1104 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for the improvement of electrocardiogram visualization, wherein the apparatus comprises:
   at least one processor; and
   a memory communicatively connected to the at least one processor, wherein the memory contains instructions configuring the at least one processor to:
   receive a plurality of electrocardiogram signals, wherein the plurality of electrocardiogram signals is generated using at least one sensor of a plurality of sensors connected to a patient;
   receive at least one transformation matrix;
   transform the plurality of electrocardiogram signals into a cardiac vector as a function of the at least one transformation matrix;
   generate a vectorcardiogram image as a function of the cardiac vector, wherein the vectorcardiogram image comprises a representation of the cardiac vector in a three-dimensional (3D) space, wherein the vectorcardiogram includes a time-dependent depiction of the cardiac vector, wherein the time-dependent depiction comprises a video generated as a function of a plurality of contiguous time slices; and
   assign at least one diagnostic label to the patient as a function of the vectorcardiogram image, wherein assigning the at least one diagnostic label utilizes an assignment machine-learning model which further comprises:
   receiving an assignment training data set, wherein the assignment training data set comprises outputs correlated to inputs, wherein the inputs comprise a plurality of data entries containing vectorcardiogram images and the outputs comprise diagnostic labels;
   sanitizing the assignment training data set, wherein sanitizing comprises:
   determining an image quality measure for each of the vectorcardiogram images of the assignment training data set;
   comparing the image quality measure for each vectorcardiogram image of the assignment training data set against a threshold value; and
   rejecting one or more vectorcardiogram images and their correlated outputs from the assignment training data set when the image quality measure of the one or more vectorcardiogram images falls below the threshold value;
   training, iteratively, the assignment machine-learning model using the assignment training data set, wherein training the assignment machine-learning model includes retraining the assignment machine-learning model with feedback from previous iterations of the assignment machine-learning model; and
   assigning the at least one diagnostic label as a function of the vectorcardiogram image using the trained assignment machine-learning model; and
   display the vectorcardiogram image in a graphical format to a healthcare professional or practitioner.

2. The apparatus of claim 1, wherein the transformation matrix is associated with a first lead system.

3. The apparatus of claim 1, wherein the memory further instructs the at least a processor to generate a diagnostic report as a function of the at least one diagnostic label and the vectorcardiogram image.

4. The apparatus of claim 1, wherein the memory further instructs the at least a processor to generate a confidence score as a function of the assignment of the at least one diagnostic label.

5. The apparatus of claim 1, wherein assigning the at least one diagnostic label to the patient comprises:
   identifying a plurality of historical vectorcardiogram images as a function of a patient profile of the patient; and
   assigning the at least one diagnostic label as a function of a comparison between a transformed cardiogram and the plurality of historical vectorcardiogram images.

6. The apparatus of claim 5, wherein the memory further instructs the at least a processor to identify a diagnostic feature as a function of the vectorcardiogram image and the plurality of historical vectorcardiogram images.

7. The apparatus of claim 1, wherein generating the vectorcardiogram image comprises:
   capturing a motion of the cardiac vector; and
   displaying the cardiac vector through an alternative lag-reconstructed ECG representation.

8. The apparatus of claim 1, wherein the vectorcardiogram image comprises a color-coded cardiac vector.

9. A method for the improvement of electrocardiogram visualization, wherein the method comprises: receiving, using at least one processor, a plurality of electrocardiogram signals, wherein the plurality of electrocardiogram signals is generated using at least one sensor of a plurality of sensors connected to a patient; receiving, using the at least one processor, at least one transformation matrix transforming, using the at least one processor, the plurality of electrocardiogram signals into a cardiac vector as a function of the at least one transformation matrix; generating, using the at least one processor, a vectorcardiogram image as a function of the cardiac vector, wherein the vectorcardiogram image comprises a representation of the cardiac vector in a three-dimensional (3D) space; wherein the vectorcardiogram includes a time-dependent depiction of the cardiac vector, wherein the time-dependent depiction comprises a video generated as a function of a plurality of contiguous time slices; assigning, using the at least one processor, at least one diagnostic label to the patient as a function of the vectorcardiogram image, wherein assigning the at least one diagnostic label utilizes an assignment machine-learning model which further comprises: receiving an assignment training data set, wherein the assignment training data set comprises outputs correlated to inputs, wherein the inputs comprise a plurality of data entries containing vectorcardiogram images and the outputs comprise diagnostic labels; sanitizing the assignment training data set, wherein sanitizing comprises: determining an image quality measure for each of the vectorcardiogram images of the assignment training data set; comparing the image quality measure for each vectorcardiogram image of the assignment training data set against a threshold value; and rejecting one or more vectorcardiogram images and their correlated outputs from the assignment training data set when the image quality measure of the one or more vectorcardiogram images falls below the threshold value; training, iteratively, the assignment machine-learning model using the assignment training data set, wherein training the assignment machine-learning model includes retraining the assignment machine-learning model with feedback from previous iterations of the assignment machine-learning model; and assigning the at least one diagnostic label as a function of the vectorcardiogram image using the trained assignment machine-learning model; and display the vectorcardiogram image in a graphical format to a healthcare professional or practitioner.

10. The method of claim 9, wherein the transformation matrix is associated with a first lead system.

11. The method of claim 9, wherein the method further comprises generating, using the at least a processor, a diagnostic report as a function of the at least one diagnostic label and the vectorcardiogram image.

12. The method of claim 9, wherein the method further comprises generating, using the at least a processor, a confidence score as a function of the assignment of the at least one diagnostic label.

13. The method of claim 9, wherein assigning the at least one diagnostic label to the patient comprises:

identifying a plurality of historical vectorcardiogram images as a function of a patient profile of the patient; and assigning the at least one diagnostic label as a function of a comparison between a transformed cardiogram and the plurality of historical vectorcardiogram images.

14. The method of claim 13, wherein the method further comprises identifying, using the at least a processor, a diagnostic feature as a function of the vectorcardiogram image and the plurality of historical vectorcardiogram images.

15. The method of claim 9, wherein generating, using the at least a processor, the vectorcardiogram image further comprises:

capturing a motion of the cardiac vector; and displaying the cardiac vector through an alternative lag-reconstructed ECG representation.

16. The method of claim 9, wherein the vectorcardiogram image comprises a color-coded cardiac vector.

* * * * *